United States Patent
Rao

(10) Patent No.: US 6,395,874 B1
(45) Date of Patent: May 28, 2002

(54) RETINAL PIGMENT EPITHELIAL PROTEIN WHICH SUPPRESSES NEUTROPHIL MACROPHAGE SUPEROXIDE GENERATION

(75) Inventor: Narsing A. Rao, Pasadena, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 08/940,577

(22) Filed: Sep. 30, 1997

Related U.S. Application Data

(60) Provisional application No. 60/027,411, filed on Sep. 30, 1996.

(51) Int. Cl.[7] .............................. C07K 7/06; C07K 7/08; C07K 9/00; C07K 14/00
(52) U.S. Cl. .................... 530/324; 530/326; 530/327; 530/328; 530/350; 530/395
(58) Field of Search ................................. 530/324, 326, 530/327, 328, 350, 395

(56) References Cited

U.S. PATENT DOCUMENTS 5,573,939 A * 11/1996 Bavik .................... 435/252.33

OTHER PUBLICATIONS

A Novel Retinal Pigment Epithelial Protein Suppresses Neutrophil Superoxide Generation. I. Characterization of the Suppressive Factor, Wu et al., Exp. Eye Res. (1996), 63, 713–725.

A Novel Retinal Pigment Epithelial Protein Suppresses Neutrophil Superoxide Generation. II. Purification and Microsequencing Analysis, Wu et al., Exp. Eye Res. (1996), 63, 727–737.

* cited by examiner

Primary Examiner—David Saunders
Assistant Examiner—Mary Beth Tong
(74) Attorney, Agent, or Firm—Fulbright & Jaworski L.L.P.

(57) ABSTRACT

This invention presents a novel protein consisting essentially of purified retinal pigment epithelial protective protein (RPP) or purified biologically active variants thereof, or immunogenic fragments or a combination of purified retinal pigment epithelial protective protein and biologically active variants thereof. Also presented are methods and kits for detecting a protein capable of inhibiting neutrophil activation in inflammatory conditions, by detecting the presence of these proteins, their immunogenic fragments, antibodies to these proteins or their fragments, or polynucleotides which encode or are translatable into these proteins or their fragments. Further disclosed are methods for isolating these proteins. Still further disclosed are methods for treating diseases associated with tissue damage due to oxygen metabolite production.

13 Claims, 13 Drawing Sheets

SEQ ID NO:1  Met Gly Ile Glu Leu Tyr Gly Tyr Tyr Xaa Xaa Ser Ala Leu Gly Glu Lys

SEQ ID NO:2  Asn Gln Asn Lys Val Gln Lys Gln Ala Asn Met His Met Gln Xaa Tyr Leu

SEQ ID NO:3  Ala Phe Ser Asn Asn Glu Ala Asp Ala Val Thr Leu Asp Gly Gly Leu Val Tyr
Glu Ala Gly Leu Ser Pro Asn

SEQ ID NO:4  Phe Leu Val Leu Asn Lys Thr Val Val Gly

SEQ ID NO:5  Gly Tyr Leu Ala Val Ala Val Val Ile Ser Leu Gly Ser

SEQ ID NO:6  Ser Ala Glu Leu Asn Lys Phe Met Gly Arg

SEQ ID NO:7  Glu Leu Val Glu Ser Gly Leu Val Ala Phe Val Ser Xaa Glu Ser
Xaa Glu Xaa Ser Ser Pro

SEQ ID NO:8  Gly Tyr Leu Ala Leu Pro Ala Phe Gln Ser Leu Gly Xaa Xaa Asn

FIG. 23

RETINAL PIGMENT EPITHELIAL PROTEIN WHICH SUPPRESSES NEUTROPHIL MACROPHAGE SUPEROXIDE GENERATION

This application claims benefit of Provisional Application Ser. No. 60/027,411 filed Sep. 30, 1996.

BACKGROUND OF THE INVENTION

Diseases related to tissue inflammation associated with oxygen metabolite production is a much studied area in the fields of medicine and biology. These diseases can include for example, stroke, arthritis, pulmonary adult respiratory distress syndrome, atherosclerosis and inflammations of the eye.

During inflammation, oxygen radicals released by phagocytes can be potentially injurious to surrounding tissues. Superoxide can be one of the most injurious species through its secondary conversion to hydrogen peroxide, hydroxyl radicals and peroxynitrite.

When this sequence of events occurs in severe inflammation, it can often lead to irreversible damage. Oxygen radical-induced lipid peroxidation products can degrade cellular membranes, but also can serve to perpetuate inflammation.

Specifically in acute intraocular inflammation, neutrophils can release a variety of agents that can be potentially toxic to surrounding tissues. Amongst these agents are reactive oxygen metabolites which includes for example, superoxide. Upon release, superoxide can dismutate spontaneously to hydrogen peroxide and through the catalysis of tissue iron, can produce hydroxyl radicals. These hydroxyl radicals can cause extensive damage to tissues. Cytotoxicity of superoxide can be manifested by its reaction with phagocyte mediated nitric oxide. The combination of these two radicals can be diffusion-limited and can produce peroxynitrite which can exert its reactivity either by reacting as an anion radical or by dissociated to a hydroxyl radical-like species. Reactive oxygen species derived from superoxide are known to those skilled in the art to inflict damage on cellular macromolecules, which can include lipids and proteins.

There are several known intracellular antioxidants which are capable of scavenging these oxygen radicals. However, disadvantages with these cellular antioxidants is that they often are unable to translocate to the extracellular space in the event of inflammation, to effectively neutralize these oxygen radicals. Intracellular antioxidant enzymes, such as superoxide dismutase, catalase, glutathione peroxidase and others, are important defenses against oxygen free radicals generated during normal cellular metabolism. These enzymes can also be found in abundant quantities in the ocular tissues. The role of reactive oxygen metabolites in the destruction of ocular tissues and amplification of the inflammatory process in uveitis, for example, has been demonstrated in animals with S-antigen induced uveo-retinitis. The extent of damage that can result from inflammation appears to be the result of an interplay between the factors that protect the ocular tissues and those that sustain the inflammation. Even though intraperitoneal injections of the antioxidant enzymes can attenuate inflammation and preserve the tissue morphology in experimental uveitis, the role of antioxidants normally found in ocular tissues in the modulation of inflammation is unclear. Antioxidants that are present intracellularly may not counter the large amounts of oxidants generated in the extracellular milieu during uveitis. The enzymes may even be inactivated by free radicals produced during the initial phases of inflammation.

For the foregoing reasons, there is a need for discovering a way to inhibit oxygen metabolite production associated with tissue inflammation related to diseases of the eye. Still further it would be advantageous to have a method for diagnosing or treating of various other diseases associated with oxygen metabolite production.

SUMMARY OF THE INVENTION

The present invention presents a protein consisting essentially of purified retinal pigment epithelial protein or purified biologically active variants thereof, or a combination of purified retinal pigment epithelial protein and biologically active variants thereof. The protein can be made from a mammal such as a rabbit, mouse, rat and human. Also disclosed are methods for purifying these proteins from retinal pigment epithelium. In particular, two proteins are disclosed, the molecular masses of these proteins are about 69-, and 75-kDa, respectively.

According to another aspect of the present invention, there is provided a high affinity monoclonal antibody which immunoreacts with retinal pigment epithelial protein or immunogenic fragments thereof. The antibody can have a Fc portion selected from the group consisting of the IgM class, the IgG class and the IgA class. There is also provided a method of making a monoclonal antibody which immunoreacts with retinal pigment epithelial protein comprising the steps of first, administering to a host retinal pigment epithelial protein in an amount sufficient to induce the production of antibodies to the retinal pigment epithelial protein form the antibody producing cells. Next, the antibody producing cells can be recovered from the host. Then, cell hybrids can be formed by fusing the antibody-producing cells to cells capable of substantially unlimited reproduction, such as myeloma cells. Then, the hybrids can be cultured and monoclonal antibodies are collected as a product of the hybrids.

There is also provided a vector containing a DNA molecule encoding retinal pigment epithelial protein and a prokaryotic or eukaryotic host cell stably transformed or transfected by the vector.

There is also provided a method of making a protein according to the present invention comprising the steps of, first culturing a microorganism transformed with DNA encoding for retinal pigment epithelial protein, and then, recovering the retinal epithelial protein or its complementary strands.

The present invention also includes a purified and isolated peptide having the Sequence I.D. No. 1: Met Gly Ile Glu Leu Tyr Gly Tyr Tyr Xaa Xaa Ser Ala Leu Gly Glu Lys, Sequence I.D. No. 2: Asn Gln Asn Lys Val Gln Lys Gln Ala Asn Met His Met Gln Xaa Tyr Leu, Sequence I.D. No. 3: Ala Phe Ser Asn Asn Glu Ala Asp Ala Val Thr Leu Asp Gly Gly Leu Val Tyr Glu Ala Gly Leu Ser Pro Asn, Sequence I.D. No. 4: Phe Leu Val Leu Asn Lys Thr Val Val Gly, Sequence I.D. No. 5: Gly Tyr Leu Ala Val Ala Val Val Ile Ser Leu Gly Ser, Sequence I.D. No. 6: Ser Ala Glu Leu Asn Lys Phe Met Gly Arg, Sequence I.D. No. 7: Glu Leu Val Glu Ser Gly Leu Val Ala Phe Val Ser Xaa Glu Ser Xaa Glu Xaa Ser Ser Pro, Sequence I.D. No. 8: Gly Tyr Leu Ala Leu Pro Ala Phe Gln Ser Leu Gly Xaa Xaa Asn. The previous sequence I.D. nos. 1–8 directly correspond to the amino acid sequences from Table II, Peak Nos. 50, 42, 52, 22, 27, 29, 34 and 24. Sequence I.D. Nos. 1–8 can be either from a natural source or from a recombinant source. Also, there is provided a high affinity monoclonal antibody which immunoreacts with this peptide. The antibody can have an Fc portion of the IgM class, the IgG class of the IgA class.

According to another aspect of the present invention, there is provided a method of detecting a protein capable of inhibiting neutrophil activation in inflammatory conditions in a sample comprising the steps of contacting the sample with a nucleic acid sequence probe capable of binding to a nucleic acid sequence encoding a retinal pigment epithelial protective protein, and detecting such binding, wherein said retinal pigment epithelial protective proteins are selected from the group consisting of retinal pigment epithelial protective proteins having molecular masses of about: 69-, and 75-kDa.

According to another aspect of the present invention, there is provided a method of detecting a protein capable of inhibiting neutrophil activation in inflammatory conditions in a sample comprising the steps of: contacting the sample with an antibody capable of binding a retinal pigment epithelial protective protein or its immunogenic fragment, and detecting such binding, wherein said retinal pigment epithelial protective protein is selected from the group consisting of retinal pigment epithelial proteins having molecular masses of about: 69-, and 75-kDa.

According to yet another aspect of the present invention, there is provided a method for detecting in a sample, an antibody capable of binding an antigen, the method comprising the steps of, first, contacting the sample with the antigen under conditions which allow the antibody to bind to the antigen, and next, detecting the binding of the antibody to the antigen; wherein the antigen is selected from the group consisting of retinal pigment epithelial protective proteins having molecular masses of about: 69-, 75-kDa, and immunogenic fragments of the foregoing.

There is also provided a kit useful for detecting an antigen, the kit comprising one or more containers containing a reagent capable of binding the antigen, said antigen is selected from the group consisting of a protein, an immunogenic fragment of the protein, a nucleotide sequence encoding the protein, a nucleotide sequence which can be translated into the protein; wherein the protein is selected from the group consisting of retinal pigment epithelial protective proteins having molecular masses of about: 69-, and 75-kDa. The reagent can be selected from the group consisting of an antibody and a nucleotide acid sequence specific for the antigen.

Also provided is kit useful for the detection of an antibody to an antigen, the kit comprising one or more containers containing the antigen, wherein the antigen is selected from the group consisting of retinal pigment epithelial protective proteins having molecular masses of about: 69-, and 75-kDa, and immunogenic fragments of the foregoing.

According to another aspect of the present invention, there is provided a method of treating diseases associated with tissue damage due to oxygen metabolite production, comprising the steps of, first, providing a sample of tissue with damage due to oxygen metabolite production from a patient; and next, administering retinal pigment epithelial protective protein, biologically active variants or immunogenic fragments to the tissue such that the oxygen metabolite production is substantially inhibited and the patient is treated. The oxygen metabolites can be superoxide, nitric oxide, peroxide, hydrogen peroxide, hydroxyl radicals, peroxynitrite or any oxygen metabolite by-products.

In a preferred embodiment, the disease or condition are diseases can be selected from the group consisting of intraocular inflammation, uveitis, macular degeneration of the eye, retinal degeneration of the eye, secondary glaucoma, cataracts, optic nerve inflammation, corneal inflammation, scleral inflammation, stroke, arthritis, atherosclerosis and any disease having inflammatory conditions where oxygen metabolites are involved in tissue damage.

Further, there is provided a method of determining an epitope of a peptide, protein, or protein homologue to which antibodies are produced in a disease or condition comprising the steps of, first providing a sample of tissue or fluid form one or more patients, wherein the sample contains antibodies directed toward a peptide, protein, or protein homologue having the epitope.

According to yet another aspect of the present invention, there is provided a method of diagnosing a disease or condition, the disease or condition having the clinical feature of antibody production against a peptide, protein, or protein homologue. The method comprises the steps of, first performing the method of determining an epitope to which antibody production is directed against a peptide, protein, or protein homologue according to the method disclosed herein.

These and other features, aspects, and advantages of the present invention will become better understood with reference to the following description and appended claims.

BRIEF DESCRIPTION OF THE DRAWINGS

FIG. 23 illustrates the amino acid sequence (SEQ ID Nos. 1–8) of retinal pigment epithelial protein.

DETAILED DESCRIPTION OF THE INVENTION

Figure 1A:
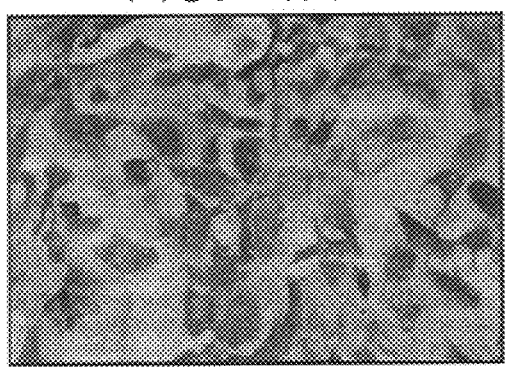
FIG. 1 illustrates a immunoperoxidase localization of cytokeratin (1A) and cellular retinaldehyde binding protein (CRALBP); (1B) in primary rat retinal pigment epithelial cell culture; and (1C) a negative control incubated with PBS in place of primary antibody.

The present invention presents a protein consisting essentially of purified retinal pigment epithelial protein (herein also referred to as RPP) or purified biologically active variants thereof, or a combination of purified retinal pigment epithelial protein and biologically active variants thereof. The protein can be made from a mammal such as a rabbit, mouse, rat and human. RPP can be found to be secreted by retinal epithelial cells (herein also referred to as RPE). Also disclosed are methods for purifying these proteins from retinal pigment epithelium. In particular, two proteins are disclosed, the molecular masses of these proteins are about 69-, and 75-kDa, respectively.

According to another aspect of the present invention, there is provided a high affinity monoclonal antibody which immunoreacts with retinal pigment epithelial protein or immunogenic fragments thereof. The antibody can have a Fc portion selected from the group consisting of the IgM class, the IgG class and the IfA class. There is also provided a method of making a monoclonal antibody which immunoreacts with retinal pigment epithelial protein comprising the steps of first, administering to a host retinal pigment epithelial protein in an amount sufficient to induce the production of antibodies to the retinal pigment epithelial protein form the antibody producing cells. Next, the antibody producing cells can be recovered from the host. Then, cell hybrids can be formed by fusing the antibody-producing cells to cells capable of substantially unlimited reproduction, such as myeloma cells. Then, the hybrids can be cultured and monoclonal antibodies are collected as a product of the hybrids.

The following references are incorporated herein by reference in their entirety, including cited references: Wu, et al., *Exp. Eye Res.*, "A Novel Retinal Pigment Epithelial Protein Suppresses Neutrophil Superoxide Generation. I. Characterization of the Suppressive Factor", 63, 713–725, 1996. Wu, et al., *Exp. Eye Res.*, "A Novel Retinal Pigment Epithelial Protein Suppresses Neutrophil Superoxide Generation. II. Purification and Microsequencing Analysis", 63, 727–737, 1996.

A novel protein secreted by cultured retinal pigment epithelial cells (RPE) was isolated and characterized. This protein, RPP, suppresses superoxide production in activated phagocytes in vitro and in vivo.

Retinal pigment epithelium, a monolayer situated between photoreceptors of the sensory retina and vascular choroid, can play a vital role in maintaining the function of metabolic and transport for the choroid and neural retina. One aspect of RPE function is associated with the normal maintenance of photoreceptors; for example, RPE can phagocytize the tips of photoreceptor outer segments, synthesize many of the enzymes participating in retinoid metabolism, and can mediate the selective uptake of fatty acids and other compounds from the bloodstream, transferring them to the photoreceptor cells.

According to one embodiment of this invention, a soluble factor was isolated from cultured rabbit and rat RPE cells that directly attenuates the PMN activation process, preventing its release of superoxide. It is called retinal pigment epithelial protective protein (RPP), since in intraocular inflammation, a protein of this nature can prevent retinal damage by inhibiting the phagocyte generation of oxygen metabolites.

I. Characterization of RPP

According to the present invention, there is provided a soluble retinal pigment epithelial protein (RPP) secreted from cultured rabbit retinal pigment epithelial (RPE) cells. It was found that RPP acts directly on neutrophils, suppressing generation of a reactive oxygen metabolite, superoxide. Preferably, this protein can be secreted specifically by cultured RPE cells and not by rabbit skin fibroblasts (FB), corneal epithelial (CE) or intact choroidal tissues. In a system with intact, noncultivated bovine RPE, this suppressive activity was also displayed. The secretion of RPP by cultured rabbit RPE cells were found not to be species-specific. Cultured rat RPE cells can also secrete RPP in a substantial quantity.

Figure 1B:
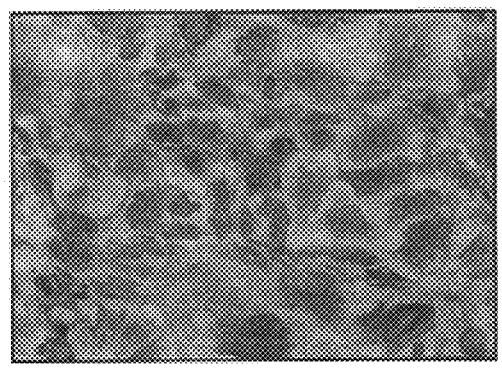
Figure 1C:
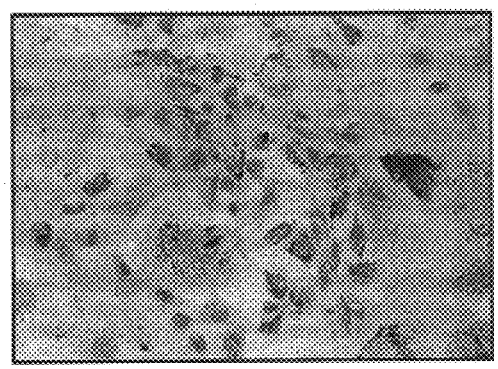
Figure 2A:
FIG. 2 illustrates immunoperoxidase localization of cytokeratin in rabbit retinal pigment epithelial cell culture.
Figure 2B:
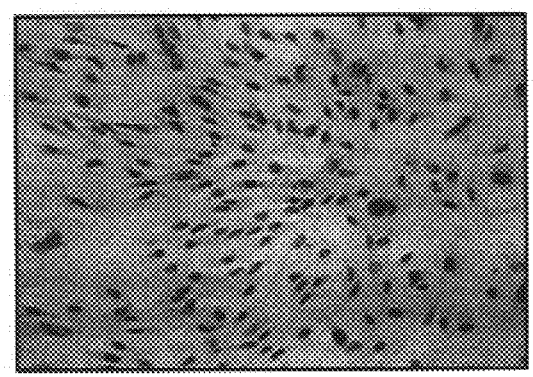

The purity of the primary culture of rat RPE cells, can be established similar to the reported characterization of these cells by McLaren et al., *Exp. Cell Res.*, 204, 311–20, 1993. The epithelial cell nature of rat RPE cells was proven by the cytokeratin staining. Cellular retinaldehyde binding protein (CRALBP) is known by those skilled in the art to specifically stain RPE cells and Müller cells. Please see Example 1 for a detailed description on characterization of retinal pigment epithelial protein. CRALBP can be used to exclude contamination of choroidal cells. In both cytokeratin and cellular retinaldehyde binding protein (CRALBP), positive stainings were associated with 100% of rat RPE cells (FIG. 1). The staining of rat RPE cultures with GFAP, an intermediate filament marker normally expressed by the Müller cells, was negative. In rabbit RPE cultures, 100% of cells stained positive with cytokeratin (FIG. 2). Preferably, immunohistochemical studies can establish the epithelial cell nature of RPE and absence of contamination from other cells, such as Müller cells, other glial cells and choroidal cells, and thus established the RPE cells being the sole source of RPP. (Please refer to Example 1 for details according to the present invention).

Inhibitory effects can be exerted with a relatively small number of RPE cells mixed in a large pool of polymorphonuclear leukocytes (PMN's). The effect of RPP in an in vitro system appears to simulate in vivo conditions of intraocular inflammation, where the RPE monolayers often can encounter massive infiltration of inflammatory cells. The secretion of RPP can be adequate to compensate effectively for massive infiltration of phagocytes at the inflammatory site. Referring to Example 1, the supernatant collected in a substantially short 30 min-period of time, produced a substantial inhibitory effect. The activity of RPP does not require a PMN-RPE cell surface contact since the supernatant without RPE cells is equally effective. However, the presence of RPE cells in the co-incubation mixture with PMN's, and therefore, a continuous supply of fresh RPP appears to be more effective than supernatant alone in which RPP was collected prior to the co-incubation with PMN's. In a crude size separation study of total supernatant proteins, the RPP activity was found to reside in the 50–300 kDa fraction.

In this in vitro system, an increase in the amount of total supernatant proteins, and therefore, an increase in the amount of RPP present in the incubation mixture, was found to increase the extent of suppression. The decrease in PMN superoxide production was strictly proportional to the amount of supernatant present and a linear correlation was obtained between the total supernatant proteins and the superoxide generated. This linear correlation can indicate that the initial concentration of RPP can play a decisive role in this sequence of events leading to the inhibition of PMN function and that this process may not be affected by the concentration of any other factors.

Under normal conditions, the cell surface of the neutrophils can be relatively smooth with a few short projections. When these cells are activated by phorbol esters or chemotactic factors, changes can begin with some granule discharge and protrusion of ruffles. Further activation can lead to disruption of the plasma membranes, formation of numerous intercellular vacuoles and, eventually, a total disintegration of the cell body. In the present embodiment of this invention, it was found that RPP was not cytotoxic to PMN's upon prolonged coincubation. Furthermore, RPP can reduce the respiratory burst-mediated destruction of PMN's, so that at the end of activation period, a larger population of PMN's may not be destroyed. According to the present invention, it was found that RPP can prevent PMN respiratory burst, thus reducing the activation-related PMN degradation.

Cycloheximide can inhibit protein biosynthesis effectively in systems that utilize ribosomes of the 80 S type. The inhibition has been shown to be in the primary initiation and chain elongation steps of biosynthetic pathways. Cycloheximide, at doses that do not alter the respiratory response of PMN's and viability of RPE cells, can substantially reduce the effect of RPP. These results suggest a requirement for de novo protein synthesis in the inhibitory action of RPP. The elimination of the activity by thermolysin and the inhibition of suppressive activity by cycloheximide also confirmed the protein nature of this suppressive factor. Since treatment with cycloheximide can be accomplished in a relatively short period of 2 hr, it also suggests that either the RPP biosynthesis itself or a co-factor is turning over at a fairly rapid rate and the RPP is a significant steady-state product.

Among the factors secreted by RPE, TGF-$\beta$ was examined in detail (Example 1). TGF-$\beta$ appears to be one of the most likely factors which could give this effect, since TGF-$\beta$ can be multifunctional and can be effective in small doses, and since neutrophils have been shown to express stable TGF-$\beta$ receptor. Retinal pigment epithelial cells have been indicated to synthesize and release TGF-$\beta$. To exclude the possibility of contaminating RPE supernatants with a trace quantity of TGF-$\beta$, the effect of TGF-$\beta$ according to the present invention, found no inhibition of PMN superoxide production.

Although the contamination of a serum component, Tf, in RPP has been eliminated by culturing the RPE cells in the serum-free medium and detecting the presence of Tf (90 kDa) by SDS-PAGE; the effect of Tf was also tested, primarily because the partial homology in peptide sequence between RPP and Tf was found (Example 1) The effects of serum, lactoferrin and Tf in the respiratory burst of PMN's have been evaluated. Lactoferrin, a Tf superfamily protein, can also bind to iron . Neutrophils plated on a serum-coated polystyrene surface can enhance fLMP-primed production of hydrogen peroxide. Both apo- and iron-saturated lactoferrin can prime PMN's to produce more superoxide in all stimuli tested, including PMA, fMLP, and opsonized zymosan. The increases observed were at least two-fold. Furthermore, apo- and iron-saturated lactoferrin, apo- and iron-saturated Tf, and albumin, all with concentrations of 10 nM, were found to give no significant effect on fLMP-stimulated PMN superoxide production; the small effects observed were all an enhancement of superoxide production rather than inhibition. According to the present invention, neither apo- nor iron-saturated Tf had an effect at lower concentrations, and there was an increase in PMN superoxide production at higher concentrations.

When RPP was added into a PMN-free system in which the superoxide was generated enzymatically, at a level comparable to that generated by activated PMN's, the scavenging of the superoxide anion by RPP was not observed. These results suggested that the scavenging of superoxide may not be a factor contributing to the observed effect, and that the RPP can be contaminated neither with SOD nor with an SOD-like compound capable of dismutating superoxide anion. These data also infer that the scavenging of PMN-derived superoxide anion by cellular SOD of RPE may not be an important factor for the effect of RPP in PMN-RPE co-culture system. Extracellular superoxide anion can be generated in a favorable microenviromnent, such as the cell interface of PMN-RPE, for this type of scavenging reaction to take place.

In the induction of respiratory burst, both fMLP and PMA can activate NADPH-oxidase through protein kinase C (PKC) pathways. Whereas fMLP can stimulate by binding to neutrophil plasma membrane receptors before proceeding to the calcium mobilization and PKC activation, PMA can act directly on PKC and can be independent of intracellular calcium increase and arachidonic acid metabolism. According to the present invention, RPP was found to suppress superoxide production of PMN's, activated either by fLMP or PMA. The interaction of RPP in signal transducing steps may intercept any of the steps in the activation cascade, including activation of PKC or other kinases, phosphorylation by PKC, and mobilization of calcium ions. The mechanism by which RPP functions remains to be elucidated.

In intraocular inflammation, such as uveitis, there can be a marked infiltration of PMN's, macrophages and lymphocytes. These inflammatory cells can release reactive oxygen metabolites upon activation, one of the species being superoxide. These reactive oxygen species can serve as microbicidal agents, but they can also be injurious to the surrounding tissues by inducing cellular peroxidation. Retinal pigment epithelial protective protein in vivo could reduce the activation responses of PMN's, thus limiting the generation of reactive oxygen metabolites from these inflammatory cells. Recognition of the role of RPP in reducing tissue injury in intraocular inflammation can depend on in vivo detection of this protein in an eye. If the superoxide inhibitory capability of RPP is operative in vivo, it could limit neutrophil and macrophage cytotoxicity while permitting the expression of cellular phagocytic function at the site of inflammation.

II. Purification and Microsequencing Analysis of RPP

In another embodiment according to the present invention, RPP was purified to homogeneity and amino acid sequenced. (Please refer to Example 2 for a detailed preferred version according to the present invention).

The retinal pigment epithelium is known to those skilled in the art, to synthesize and release a broad array of proteins, that may function to protect the structure and metabolism of photoreceptors. Using the $^{35}$S methionine labeling and two-dimensional gel electrophoresis, at least 200 different proteins were detected in the cultured human RPE cells. Retinal pigment epithelium appears to synthesize specific protein for certain specific functions.

According to the present invention, RPP was characterized by purification and microsequencing analysis. Example 2 shows the preferred embodiment of this invention with regard to isolating and purifying RPP. In the purification of cellular secretory proteins, where a large volume is normally processed to obtain a sufficient quantity of purified protein, an appropriate choice for the initial large capacity chromatography preferably is an open column anion exchange chromatography, which can lead to an efficient separation, concomitant concentration and retention of activity. By combining the initial high capacity anion exchange chromatography with the subsequent secondary microseparation AE- and RP-HPLC according to the preferred embodiment of this invention, a pure RPP doublet of 69/75 kDa was isolated without any other contamination (FIG. 14).

Figure 14:
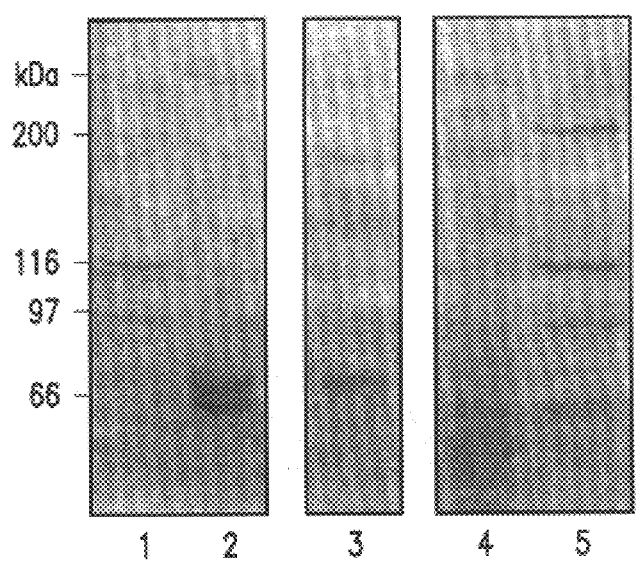
FIG. 14 illustrates SDS-page analysis of RPP at different stages of purification.

With respect to FIG. 14, inhibitory activity was found to reside in this doublet, with both bands being equally active. Preferably, according to one aspect of the present invention, to obtain unequivocal results in sequencing, state-of-the-art mass spectrometric analysis was used to determine the homogeneity of the tryptic digests before subjecting them to Edman degradation. From both bands, the microsequencing gave a total of eight polypeptide sequences; Sequence I.D. No. 1: Met Gly Ile Glu Leu Tyr Gly Tyr Tyr Xaa Xaa Ser Ala Leu Gly Glu Lys, Sequence I.D. No. 2: Asn Gln Asn Lys Val Gln Lys Gln Ala Asn Met His Met Gln Xaa Tyr Leu, Sequence I.D. No. 3: Ala Phe Ser Asn Asn Glu Ala Asp Ala Val Thr Leu Asp Gly Gly Leu Val Tyr Glu Ala Gly Leu Ser Pro Asn, Sequence I.D. No. 4: Phe Leu Val Leu Asn Lys Thr Val Val Gly, Sequence I.D. No. 5: Gly Tyr Leu Ala Val Ala Val Val Ile Ser Leu Gly Ser, Sequence I.D. No. 6: Ser Ala Glu Leu Asn Lys Phe Met Gly Arg, Sequence I.D. No. 7: Glu Leu Val Glu Ser Gly Leu Val Ala Phe Val Ser Xaa Glu Ser Xaa Glu Xaa Ser Ser Pro, Sequence I.D. No. 8: Gly Tyr Leu Ala Leu Pro Ala Phe Gln Ser Leu Gly Xaa Xaa Asn. The previous sequence I.D. nos. 1–8 directly correspond to the amino acid sequences from Table II, Peak Nos. 50, 42, 52, 22, 27, 29, 34 and 24. Three of the sequences shared some degree of homology with the Tf family of proteins, and the other five sequences did not match any sequence in the database (BLAST Program, National Center for Biotechnology Information, National Library of Medicine, National Institute of Health, Bethesda, Md.).

Since a partial homology in the amino acid sequence between RPP and Tf family proteins was revealed, the similarity and dissimilarity in other aspects of these two proteins were also compared. The known Tf family proteins include the iron transport protein, Tf (serotransferrin) from the serum, ovotransferrin from hen egg white, lactotransferrin (lactoferrin) primarily from human milk but also present in various biological fluids, and melanotransferrin from the membranes of meloanocarcinoma cells. Tfs typically are glycoproteins of approximately 90 kDa and can reversibly bind to two $Fe^{3+}$ per molecule of Tf. The biological functions of Tf, including iron transport and bacterial defense mechanisms, can be derived from its strong affinity for iron. The effect of Tf family proteins in the respiratory burst of neutrophils has been tested in the past. The whole serum, Tf (serotransferrin), and lactoferrin (lactotransferrin), were all found to give either no significant effect or an increase, rather than a decrease in PMN superoxide production, stimulated by either phorbol myristate acetate, fMLP or opsonized zymosan. According to the present invention, neither apo- nor iron-saturated Tf gave any significant effect at lower concentrations and there was a substantial increase in PMN superoxide production at higher concentrations (see Example 1). The RPP appears to exert its activity by directly suppressing the respiratory burst of PMN's during activation. Typically, respiratory burst activators, either with (fMLP) or without (phorbol myristate acetate) the prior neutrophil receptor binding, can activate NADPH-oxidase through protein kinase C.

Preferably, the possibility of contamination of serum proteins can be excluded by exhaustive washings, or culturing the RPE cells in serum-free medium for at least 48 hr before collecting the supernatants (Example 2). Following these manipulations, the SDS-PAGE of the collected supernatant indicated the absence of the 67 kDa BSA band, a major protein in the tissue culture serum. The serum contamination, if any, was doubly excluded by passing the RPE supernatant proteins through the anion exchange column. No serum components were found at an elution volume of 375 ml, where the active protein was collected.

Typically, bovine Tf can separate into four bands (subunits) by conventional DEAE-Sephadex anion exchange chromatography with NaCl gradient. These four bands were completely resolvable with only one band appearing in one fraction and the glycosylation is not the cause of this molecular weight heterogeneity. Anion exchange chromatography was performed and found the RPP doublet (FIG. 14) was found to be inseparable under any gradient. The individual fractions from the active peak (FIG. 11, Fr. III) consistently gave the same doublet with only a slight variation in relative concentrations of two bands between fractions. Furthermore, this doublet was not resolvable even with the Pharmacia's SMART system (AE-HPLC) or a microcapillary RP-HPLC.

Under SDS-PAGE and reducing conditions, RPP can be seen as a doublet with an estimated MWt of 69/75 kDa. The biological activity of both bands is comparable. Under nonreducing conditions, one broad band centered at 90 kDa was obtained. Therefore, the doublet does not represent two subunits of RPP, rather it appears to be either two polymorphic forms of closely related structures, or the native and the deglycosylated form of RPP. It is well known to those skilled in the art, that the tripeptide, Asn-Xaa-Thr/Ser represents the code sequence for possible N-glycosidically linked sugar groups in the protein. The presence of such a sequence, however, does not necessarily indicate the occurrence of glycosylation. One such sequence can be seen in Table 2 (Sequence #52).

The similarity search indicated that the peptides #50, #27 and #34 show a moderate to high degree of homology with Tf family proteins from different species. The Tf family proteins with known amino acid sequence include serotransferrin, ovotransferrin, lactotransferrin and melanotransferrin. All of these show extensive homology to one another. In a comparative study, all of the available Tf amino acid sequences from eight species were compared, and a high degree of conservation was found in both the sequences and the $Fe^{+3}$ binding. These findings can explain our search results that the peptides #52 and #27 show the same degree of homology to various species in lactotransferrin, serotransferrin and ovotransferrin; except in. peptide #27, the homology to either horse serotransferrin or chick ovotransferrin is not found, possibly because the complete sequences for these two Tfs are not yet available.

In intraocular inflammation, the activated PMN's and macrophages can secrete various microbicidal agents, including superoxide, which are potentially cytotoxic to the surrounding tissues. If the inhibitory effect of RPP can be operative in vivo, RPP could alleviate these cytotoxic effects by regulating the activation processes of PMN's. Using anti-RPP antibodies, the expression of RPP in vivo can indicate that the RPP is expressed in low levels in normal conditions in both Lewis rats and albino rabbits and these levels appear to be upregulated in inflammatory conditions. During inflammation, the RPP was found to be abundantly expressed in RPE, with no detectable expression in retina or choroid. These findings can suggest that the RPP is synthesized in vivo in RPE cytoplasms, and it is not a blood component. Serotransferrin, is known by those skilled in the art, to be synthesized by photoreceptor cells but not by RPE.

III. Inhibition of Superoxide Generation by RPP

Typically, RPP can suppress the production of superoxide in experimental uveitis, as noted in vitro studies. Furthermore, RPP can also decrease the amount of protein leakage into the ocular cavities. When purified RPP was injected, similar suppression of superoxide was seen in the vitreous. (Refer to Example 3 for details in its entirety). The difference was not as significant as with the crude preparation. This can be due to partial loss of activity of the protein during the purification process.

Usually the leakage of plasma and the migration of cells occur concurrently during an inflammatory process. Exceptions can include IL-1-induced inflammation, where only cell infiltration occurs without any vascular leakage. Typically, RPP can suppress leakage of protein without affecting cell recruitment.

Intravitreal injection of bacterial LPS can result in an inflammatory response characterized by altered vascular permeability and extravasation of inflammatory cells, primarily PMN's. PMN's typically can be responsible for increased permeability occurring in LPS-induced inflammation, especially during the latter part. Increase in vascular permeability in LPS-induced inflammation can be prevented when PMN's are depleted. The increase in vascular permeability seen in the presence of PMN's can be attributed to the lysosomal enzymes, particularly elastase and collagenase, released from these cells during inflammation. Lysosomal enzymes typically are known to those skilled in the art to affect the integrity of the basement membrane in the walls of blood vessels. According to the present invention, vascular leakage was reduced which can most likely be attributed to RPP affecting the release of these enzymes in addition to suppressing the superoxide production.

Antiproteinases, such as proteinase inhibitor, that are present in the tissues typically are known by those skilled in the art to be able to counter the elastase released by the PMN's. However, the oxidants generated by these cells inactivate the antiproteinases. Since the presence of RPP resulted in a reduction of superoxide, the antiproteinases might not be inactivated by RPP and thus the RPP may be able to prevent vascular damage mediated by the enzymes released from PMN's.

Thus, RPP could function as an anti-inflammatory protein and could protect retina and other structures from inflammation-mediated damage.

IV. Novel Epitope Expressed in Retinal Pigment Epithelium

To further establish the localization and distribution of RPP in situ, monoclonal antibodies (mAb) and polyclonal antibodies (pAb) were generated to RPP (see Example 4 for a detailed preferred version of isolating mAbs and pAbs. These antibodies were found to immunoblot to the 75 kD protein previously identified as RPP from the RPE culture supernatant. When co-incubated with RPE cells, the antibodies also abolished the RPP activity, negating the inhibitory effect displayed by RPP on PMN superoxide production. With the mAb in particular, cultured RPE cells were found to stain throughout the cytoplasm and the RPE cells in the eyes were immunolabelled intensely and specifically by the mAb. No other ocular tissue or nonocular tissue was found to be immunolabelled by this mAb.

Typically, RPE-related mAbs can be generated by immunizing either whole RPE cells or a crude preparation of RPE membrane fractions. In these preparations, the mAbs can be developed with unspecified proteins, to obtain the entire panel of mAbs, and a selection of RPE-specific or pseudo RPE-specific clones can be made at this step. The selected clone can then be transblotted to total RPE proteins to determine the molecular weight of the protein cross-reacted to the mAb. However, a disadvantage with this method can be that the functions of most of these proteins may not be elucidated, which can be due to the crude nature of the immunogens utilized, which can compromise the specificity of the clone. For example, an RPE-specific clone (72 kD) isolated by immunizing RPE plasma membranes was found also to crossreact with lens tissues, and a 32 kD reacting clone from the immunization of RPE detergent extracts also stained several other epithelia in the rat eye. These mAbs once isolated typically were used as a marker in developmental studies of RPE and retina.

According to a preferred embodiment of this invention, a structurally and functionally well-defined RPE-secreted protein can be used, and mAbs can be generated to search for a clone(s) which can cross-reacts specifically with this RPE protein. More preferably, purified RPP can be used as an immunogen.

Preferably, according to one embodiment of the present invention, in the generation of antibodies, anion exchange column-purified RPP can be used as the immunogen. During purification of RPP, crude RPE supernatant proteins can be separated with DEAE SEPHAROSE® CL-6B column (an anion exchanger), and the biologically active fraction can be identified from the eluted material. Referring now to Example 3, SDS-PAGE analysis of this fraction revealed a major well-resolved 69/75-kD doublet with two more minor bands located near the 30 to 40 kD region. Most of the proteins present originally in the total RPE supernatant had been eliminated. Subsequently, secondary purification can be carried out using microseparation high performance liquid chromatography (HPLC) to further remove the two contaminating minor 30 to 40 kD bands, leaving the 69/75-kD doublet as the only constituent. Further separation of the two proteins in the doublet was not possible either by anion exchange HPLC or by microcapillary reversed phase HPLC. In the preparation of mAbs according to the present invention, preferably, HPLC-purified samples should not be used for the following reasons: 1) The microseparation HPLC can offer state-of-art separation; however, the yield from a single injection typically is in $\mu$g quantities, and it would be extremely labor intensive to collect enough pure RPP to immunize 5 Balb/c mice; 2) Although the HPLC can give a two-to threefold increase in chemical purity, the biological activity per $\mu$g of protein may not be increased, which could indicate possible conformational changes in secondary or tertiary protein structure following this manipulation.

Figure 18:
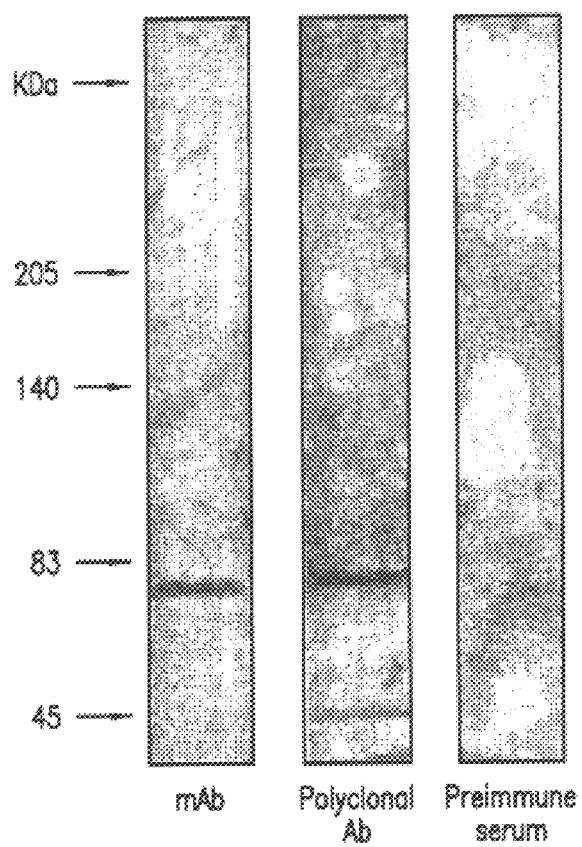
FIG. 18 illustrates a SDS-PAGE and immunoblot analysis of RPE supernatant proteins; the total supernatant proteins from the cultured rabbit RPE cells were separated on SDS polyacrylamide gels, electrophoretically transferred onto a polyvinylidene difluoride membrane and incubated with different primary antibodies.
Figure 20:
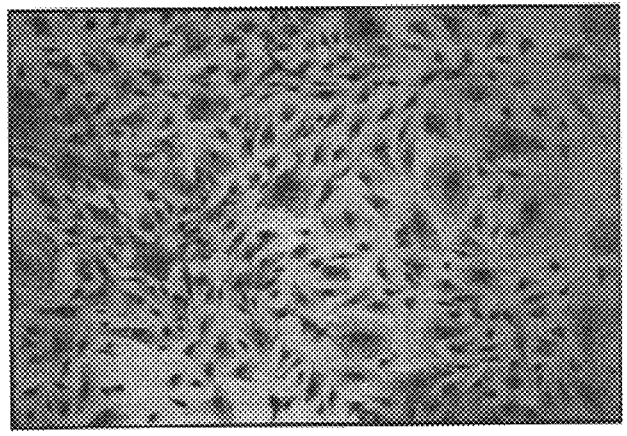
FIG. 20 illustrates immunoperoxidase analysis of rat RPE culture.

Referring now to Example 3, in the immunoblot analysis of antibodies, both the mAb and the pAb recognized a single antigen in the electrophoretically separated total RPE-secreted proteins. This band corresponds to the upper band of the 69/75 kD doublet, components of purified active. The lower 69 kD band of this doublet apparently was not recognized by the pAb and, therefore, was not recognized by the mAb derived from it (FIG. 20). In the chromatographically pure RPP samples, the upper 75 kD band was always dominant; the 69 kD band, however, could not be eliminated in any separation procedure attempted. Furthermore, from the microsequencing analysis, both 75 and 69 kD bands were found to contain the same polypeptide sequences, the small difference in molecular weight presumably arising from some minor chemical modification on one of the proteins. Additionally, the pAb also recognized the minor 40 kD protein present as one of the minor constituents in the immunogen preparation (FIG. 18).

According to one aspect of the present invention, a method is disclosed in generating antibodies to RPP, and not to other RPE proteins. Both the pAb and the mAb were rigorously evaluated for their capability to block RPP activity. A quantity of 0.3 to 0.4 $\mu$g of RPP present in the RPE culture supernatants reduced the superoxide production in 8 to 9×10$^5$ PMN's by 60 to 70%. This inhibitory effect was abolished by the pAb. The mAb, under the conditions tested, abolished the RPP effect by 85 to 90%. It is presumed that the reaction between RPP and mAbs is a reversible reaction, so that at 37° C., this value represents a steady-state product concentration of the RPP mAb complex. The binding efficiency between antigen and antibody typically will probably be different for each antigen-antibody pair. Although the complex formation at 4° C. has been indicated to decrease the rate of dissociation of antigen antibody complex, it is difficult to adapt this condition for the present assay involving PMN's.

According to the present invention, RPP was found to be localized throughout the cytoplasm of RPE cells, suggesting that the biosynthetic machinery is located in cytoplasm. Variation in staining intensities between plasma membranes and cytoplasm was not noted. Further localization of RPP production in the intracellular site typically can be detected by immunoelectron microscopy. In the localization of RPP in the eye, the release of RPP outside the RPE domain was not noted. The reason for this observation could be twofold: 1) the concentration of RPP released is much smaller than at the site of production; 2) the diffusion of RPP away from the site of production is facilitated by its hydrophilicity and solubility.

The specificity of the RPP-mAb binding site preferably shows the antibody reacting only with the RPE cells within the eye and not with any other ocular or nonocular tissues. This antibody can be useful in defining the role of RPP in inflammation as well as elucidating the mechanism of RPP action on PMN's. Moreover, there is preliminary indication from the staining pattern that intravitreal injection of lipopolysaccharide may have caused up-regulation of RPP production.

Referring now to FIG. 18, there is illustrated SDS-PAGE and immunoblot analysis of RPE supernatant proteins. The total supernatant proteins from the cultured rabbit RPE cells were separated on SDS polyacrylamide gels, electrophoretically transferred onto a polyvinylidene difluoride membrane and incubated with different primary antibodies. Specifically bound antibodies were detected by biotinylated goat anti-mouse Ig and visualized with avidin-biotin complex and 3,3-diaminobenzidine tetrachloride/NiCl2 solution. Lane 1, monoclonal antibody; Lane 2, polyclonal antibody; Lane 3, preimmune serum. The monoclonal antibody reacted with a single antigen of 75 kD; polyclonal antibody also reacted with the 75 kD antigen as a major band, and a minor band at 40 kD was also seen. Preimmune serum recognized no antigen in this panel of proteins.

Figure 19:
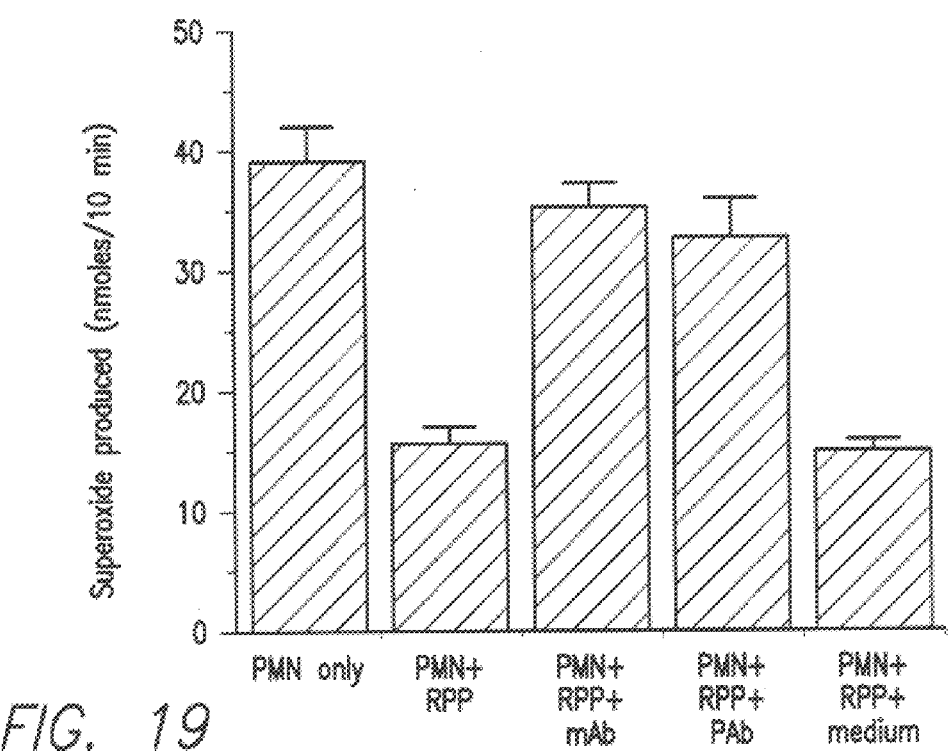
FIG. 19 graphically presents reversal of RPP activity by antibodies superoxide production PMN only; PMN+RPP; PMN+RPP+mAb; PMN+RPP+pAb; PMN+RPP+medium.

Referring now to FIG. 19, there is illustrated reversal of RPP activity by antibodies. RPP in the cultured RPE supernatant (1 ml, containing approximately 0.3 ul of RPP) were co-incubated with either 60 ul of monoclonal antibody or 2 $\mu$l of polyclonal antibody for 45 min. Rabbit peritoneal PMN's, 9.8×10$^5$ were used for the assay. For the controls without antibodies, 60 $\mu$l of culture medium containing 1% of serum and 1 ug of irrelevant mouse Ig were added to RPP in place of antibodies (see the bar indicated as PMN+RPP+ medium). The respiratory burst of PMN's was stimulated by 0.5 AM fMLP and the superoxide production was assayed by the superoxide dismutase-inhibited reduction of cytochrome C. The results, expressed as nmoles of superoxide generated, are shown as mean +/−SD of 3–5 experiments.

Referring now to FIG. 20, there is illustrated immunoperoxidase analysis of rat RPE culture. Rabbit RPE cells were grown on the chamber slides to near confluence. The RPE cells were stained with monoclonal antibody as the primary antibody and biotinylated goat anti-mouse Ig as the secondary antibody. Positive staining was seen throughout the cytoplasm of these cells (magnification, ×160).

Figure 21:
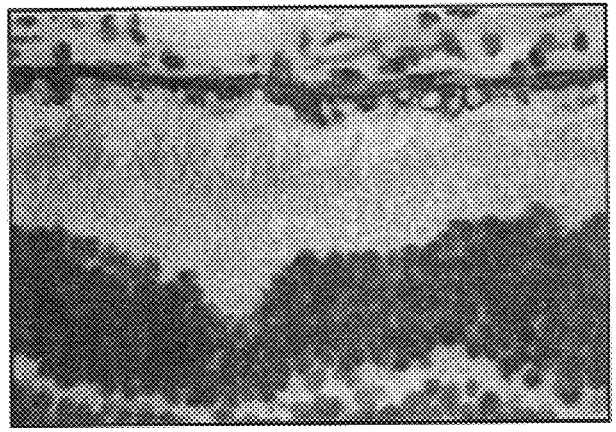
FIG. 21 illustrates immunoperoxidase staining of a frozen section of the posterior segment of New Zealand white rabbit eye; the sections were incubated with monoclonal antibody as the primary antibody, followed by a biotinylated goat anti-mouse Ig as the secondary antibody.

Referring now to FIG. 21, there is illustrated immunoperoxidase staining of a frozen section of the posterior segment of New Zealand white rabbit eye. The sections were incubated with monoclonal antibody as the primary antibody, followed by a biotinylated goat anti-mouse Ig as the secondary antibody. Note the intense and specific staining of RPE (magnification, ×250). The control sections stained with preimmune serum or PBS in place of primary antibody were totally negative.

Figure 22:
FIG. 22 illustrates Immunoperoxidase analysis of a frozen section of New Zealand white rabbit eye. Tissue was stained with monoclonal antibody as the primary antibody followed by the biotinylated goat anti-mouse Ig as the secondary antibody.

Referring now to FIG. 22, there is illustrated immunoperoxidase analysis of a frozen section of New Zealand white rabbit eye. Tissue was stained with monoclonal antibody as the primary antibody followed by the biotinylated goat anti-mouse Ig as the secondary antibody. Arrow indicates the specific staining on the RPE cells. At the same section, ciliary body is devoid of staining (magnification, ×100).

V. Further Description of Embodiments of the Present Invention

According to the present invention, therefore, there is also provided a protein consisting essentially of purified retinal pigment epithelial protective protein or purified biologically active variants thereof, or a combination of purified retinal pigment epithelial protective protein and biologically active variants thereof. This protein can be purified from natural sources such as rabbit, mouse, rat or human, or can be made by recombinant techniques as will be understood by those skilled in the art with reference to the disclosure herein. Further, there is provided a protein recognized by a monoclonal antibody having affinity to retinal pigment epithelial protective protein or a variant of retinal pigment epithelial protective protein.

Still further, the present application claims both the native and synthetic amino acid and nucleotide sequences. Unless otherwise modified, the term "protein" as used herein encompasses both native and synthetic polypeptides and peptide. Synthetic protein includes recombinant and chemically synthesized protein. Unless otherwise indicated, the term "retinal pigment epithelial protective proteins" include both the native and synthetic versions of the proteins.

The term "nucleotide sequence" includes both the DNA and RNA sequences. For example, the nucleotide sequence for a particular retinal pigment epithelial protective protein ("retinal pigment epithelial protective nucleotide sequence") include the gene ("retinal pigment epithelial protective gene") encoding the protein, its complementary DNA, and the RNA corresponding to the foregoing; also included are messenger RNA encoding for the retinal pigment epithelial protective protein, its complementary RNA, and the DNA corresponding to the foregoing. Further, as used in this application the nucleotide sequences include: (1) the DNA sequences encoding the retinal pigment epithelial protective proteins, (2) the nucleotide sequences (which may be RNA or DNA) complementary to the foregoing sequences, (3) the corresponding RNA sequences to the DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methyl-cytosine replacing cytosine, and (5) nucleotide sequences that are for example, within a 20% and preferably 10% variance to the foregoing nucleotide sequences.

Since nucleotide codons are redundant, also within the scope of this invention are equivalent nucleotide sequences which include: nucleotide sequences which code for or can be translated into the retinal pigment epithelial protective proteins, their protein variants, functional equivalents, or derivatives. These nucleotide sequences may also be used in the practice of the invention.

In addition to the above, retinal pigment epithelial protective nucleotide sequences also include: (1) nucleotide sequences that are capable of hybridizing to the coding sequences of the respective nucleotide sequences, under stringent hybridization conditions, and (2) fragments of or mutagenized nucleotide sequences of those disclosed herein which can encode or can be translated into proteins having substantially the same biological characteristics/activities of the respective retinal pigment epithelial protective proteins.

As herein defined, a "biological sample" can be a biological fluid or tissue sample. Examples of a biological fluid sample include: blood, serum, plasma, tear, milk, urine, and cerebro-spinal fluid. Examples of a biological tissue sample include tissue samples from the eyes, the lungs, and the central nervous system. Thus, for example, immunohistochemical assay can be conducted on these tissue samples. Preferably, these samples are from mammals.

Also there is provided a high affinity monoclonal antibody which innumoreacts with retinal pigment epithelial protective protein or to a fragment thereof. The antibody can have an Fc portion selected from the group consisting of the IgM class, the IgG class and the IgA class.

There is also provided a method of making a monoclonal antibody which immunoreacts with retinal pigment epithelial protective protein comprising the steps of, first, administering to a host retinal pigment epithelial protective protein in an amount sufficient to induce the production of antibodies to the retinal pigment epithelial protective protein from the antibody-producing cells; second, recovering the antibody-producing cells from the host; third, forming cell hybrids by fusing the antibody-producing cell to cells capable of substantially unlimited reproduction; fourth, culturing the hybrids; and fifth, collecting the monoclonal antibodies as a product of the hybrids.

There is also provided a vector containing a DNA molecule encoding retinal pigment epithelial protective protein, as well as a prokaryotic or eukaryotic host cell stably transformed or transfected by the vector, made according to techniques understood by those with skill in the art with reference to the disclosure herein.

Further, there is provided a method of making the retinal pigment epithelial protective protein or its biological variants comprising the steps of, first culturing a microorganism transformed with DNA encoding for retinal pigment epithelial protective protein; and then, recovering the retinal pigment epithelial protective or its complementary strands.

The terms "retinal pigment epithelial protective proteins", as used in relation to proteins include the respective proteins described in the Example section, below, most preferably retinal pigment epithelial protective proteins obtainable from the isolation methods of the Example section below, and: (1) protein variants of these proteins; e.g. these protein variants may contain amino acid sequences that have for example, at least 90% or more preferably at least 95% of their amino acids matching the sequences of the retinal pigment epithelial protective proteins, excluding their signal peptides; (2) the functional equivalents of these proteins and their variants, respectively; and (3) the derivatives, including fragments, of the retinal pigment epithelial protective proteins and their variants, respectively.

Preferably, when used in an immunoassay, these proteins are immunoreactive (the immunoreactive retinal pigment epithelial protective proteins are also referred to as "retinal pigment epithelial protective antigens") with antibodies directed to retinal pigment epithelial protective protein but not detectably immunoreactive with non-retinal pigment epithelial protective antibodies found in a biological sample.

The variants can result from, e.g. substitution, insertion, or deletion of the amino acid sequences of the retinal pigment epithelial protective proteins. The derivatives of the proteins and their variants, include fragments of these proteins and their immunogenic epitopes.

Two amino acid sequences are functionally equivalent if they have substantially the same biological activities such as the ability to provoke inhibition of cellular response of neutrophils due to oxygen metabolite production. The proteins may be fused to other proteins, for example, signal sequence fusions may be employed in order to more expeditiously direct the secretion of the retinal pigment epithelial protective proteins.

Substitutional variants of the proteins disclosed herein are those in which at least one residue in the disclosed sequences has been removed and a different residue inserted in its place. Preferably, the amino acid change is conservative. Thus, modifications of the retinal pigment epithelial protective proteins' primary amino acid sequences also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of retinal pigment epithelial protective proteins. They include variants completely lacking in glycosylation (unglycosylated) and variants having at least one less glycosylated site than the native form (deglycosylated) as well as variants in which the glycosylation has been changed.

Recombinant retinal pigment epthelial protective fusion proteins may be produced in *Escherichia coli* (*E. coli*). These proteins can be used to immunize a mammal to generate antisera. The genes for the retinal pigment epithelial protective proteins may be cloned into a plasmid vector which is then used to transform *E. coli*.

Sequence analysis of the structural genes may be conducted to determine their number of bases and amino acids. Immunoblot and immunohistochemical studies may be used to determine antisera to each of the retinal pigment epithelial protective proteins. The sequence analysis, immunohistochemical and immunoblot studies may be conducted using methods known in the art.

The invention includes polynucleotides encoding the retinal pigment epithelial protective proteins. These polynucleotides include DNA and RNA sequences which encode the protein. As discussed previously, it is understood that all polynucleotides encoding all or a portion of each of the retinal pigment epithelial protective proteins are also included herein, so long as they exhibit a function of the retinal pigment epithelial protective protein, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid nonspecific binding, it is possible, for example, to allow the autoradiographic visualization of a specific DNA clone by the hybridization of the target DNA to that single probe in the mixture which is its complete complement {Wallace, et aL, *Nucleic Acid Research*, 9:879 (1981)}.

Alternatively, an expression library can be screened indirectly for the retinal pigment epithelial protective peptides having at least one epitope using antibodies to the retinal pigment epithelial protective proteins. Such antibodies can be either polyclonally or monoclonally derived and used to detect expression product indicative of the presence of retinal pigment epithelial protective DNA.

The development of specific DNA sequences encoding the retinal pigment epithelial protective proteins can also be obtained by: (1) isolation of a double-stranded DNA sequence from the genomic DNA, and (2) chemical manufacture of a DNA sequence to provide the necessary codons for the polypeptide of interest.

DNA sequences encoding the retinal pigment epithelial protective proteins can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of an retinal pigment epithelial protective protein. Prokaryotic hosts may include Gram negative as well as Gram positive bacteria, such as *E. coli, S. typhimurium,* and *Bacillus subtilis.*

A recombinant DNA molecule coding for an retinal pigment epithelial protective protein can be used to transform a host using any of the techniques commonly known to those of ordinary skill in the art. Especially preferred is the use of a plasmid containing the retinal pigment epithelial protective protein coding sequence for purposes of prokaryotic transformation. Where the host is prokaryotic, such as *E coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, the retinal pigment epithelial protective nucleotide sequence may be inserted into a recombinant expression vector. The term "recombinant expression vector" refers to a plasmid, virus or other vehicle known in the art that has been manipulated by insertion or incorporation of retinal pigment epithelial protective genetic sequence. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported. Biologically functional DNA vectors capable of expression and replication in a host are known in the art. Such vectors are used to incorporate DNA sequences of the invention.

Methods for preparing fused, operably linked genes and expressing them in bacteria are known to those skilled in the art. The genetic constructs and methods described therein can be utilized for expression of the retinal pigment epithelial protective proteins in prokaryotic hosts.

Examples of promoters which can be used in the invention are: rec A, trp, lac, tac, and bacteriophage lambda $p_R$, or $p_L$. Examples of plasmids which can be used in the invention are listed in Sambrook, et al. {*Molecular Cloning,* Cold Spring Harbor Laboratories, 1982}.

Antibodies provided in the present invention are immunoreactive with one or more retinal pigment epithelial protective proteins. These antibodies can be polyclonal antibodies or monoclonal antibodies. Polyclonal antibodies can be produced according to methods known in the art, such as, vaccinating an animal with an retinal pigment epithelial protective protein, collecting and purifying the animal's antisera directed against the retinal pigment epithelial protective protein. Monospecific polyclonal antibodies can also be produced using methods known in the art. Antibody which consists essentially of pooled monoclonal antibodies with different epitopic specificities, as well as distinct monoclonal antibody preparations are also provided. Monoclonal antibodies are made from antigen containing fragments of the protein by methods well known in the art {Kohler, et al., *Nature,* 256:495 (1975); *Current Protocols in Molecular Biology,* Ausubel, et al., ed., (1989)}. For example, monoclonal antibodies can be produced by the method of Kohler and Milstein {*Nature,* 256:495–497 (1975)} by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps.

The term antibody, or immunoglobulin, as used in this invention includes intact molecules as well as fragments thereof, such as Fab, F(ab')$_2$, Fv, and single chain antibody ("SCA") which are capable of binding an epitopic determinant on a retinal pigment epithelial protective protein. SCA is a genetically engineered fused single chain molecule containing the variable region of the light chain and the variable region of the heavy chain linked by a suitable polypeptide linker. Methods for making these fragments are known in the art, see e.g., Harlow and Lane, *Antibodies: A Laboratory Manual,* Cold Spring Harbor Laboratory, New York (1988).

As discussed previously, minor modifications of the retinal pigment epithelial protective proteins' primary amino acid sequences may result in proteins which have substantially equivalent function compared to the retinal pigment epithelial protective proteins described herein. Such modifications may be deliberate, as by site-directed mutagenesis, or may be spontaneous. All proteins produced by these modifications are included herein as long as retinal pigment epithelial protective protein functions exist.

Isolation and purification of microbially expressed proteins, or fragments thereof, provided by the invention, may be carried out by conventional means including preparative chromatography and immunological separations involving monoclonal or polyclonal antibodies.

For purposes of the invention, an antibody or nucleic acid probe specific for a retinal pigment epithelial protective protein may be used to detect the presence of the respective retinal pigment epithelial protective protein (using antibody) or polynucleotide (using nucleic acid probe) in biological samples. Any specimen containing a detectable amount of the retinal pigment epithelial protective antigen or polynucleotide can be used. Preferred specimens of this invention are a biological fluid or tissue sample. Preferred examples of a biological fluid sample include: blood, serum, plasma, tear, milk, urine, and cerebro-spinal fluid.

When the cell component is nucleic acid, it may be necessary to amplify the nucleic acid prior to binding with a retinal pigment epithelial protective specific probe. Preferably, PCR is used, however, other nucleic acid amplification procedures such as ligase chain reaction ("LCR"), ligated activated transcription ("LAT") and nucleic acid sequence-based amplification ("NASBA") may be used.

Alternatively, an retinal pigment epithelial protective protein can be used to detect antibodies to the respective retinal pigment epithelial protective protein in a specimen. The retinal pigment epithelial protective proteins of the invention are particularly suited for use in immunoassays in which they can be utilized in liquid phase or bound to a solid phase carrier. In addition, the retinal pigment epithelial protective proteins used in these assays can be detectably labeled in various ways.

Examples of immunoassays which can utilize the retinal pigment epithelial protective proteins are competitive and noncompetitive immunoassays in either a direct or indirect format. Examples of such immunoassays are the radioimmunoassay ("RIA"), the sandwich (immunometric assay) and the Western blot assay. Detection of antibodies which bind to one or more of the retinal pigment epithelial protective proteins of the invention can be done utilizing immunoassays which run in either the forward, reverse, or simultaneous modes, including immunohistochemical assays on biological samples. The concentration of an retinal pigment epithelial protective protein which is used will vary depending on the type of immunoassay and nature of the detectable label which is used. However, regardless of the type of immunoassay which is used, the concentration of the retinal pigment epithelial protective proteins utilized can be readily determined by one of ordinary skill in the art using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to an retinal pigment epithelial protective protein may be present in various biological samples. Any sample containing a detectable amount of antibodies to an retinal pigment epithelial protective protein can be used. Preferred specimens of this invention are: a biological fluid or tissue sample. Preferred examples of a biological fluid sample include: blood, serum, plasma, tear, milk, urine, and cerebrospinal fluid.

The antibodies of the invention, preferably monoclonal antibodies, directed toward an retinal pigment epithelial protective protein, are also useful for the in vivo detection of antigen. The detectably labeled antibody is given in a dose which is diagnostically effective. The term "diagnostically effective" means that the amount of detectably labeled monoclonal antibody is administered in sufficient quantity to enable detection of retinal pigment epithelial protective antigen for which the antibodies are specific.

The concentration of detectably labeled antibody which is administered should be sufficient such that the binding to those cells, body fluid, or tissue having one or more of the retinal pigment epithelial protective proteins is detectable compared to the background. Further, it is desirable that the detectably labeled antibody be rapidly cleared from the circulatory system in order to give the best target-to-background signal ratio.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a binding reagent which binds one or more of the retinal pigment epithelial protective proteins, such as an antibody. A second container may further comprise one or more of the retinal pigment epithelial protective proteins. The constituents may be present in liquid or lyophilized form, as desired.

In the above discussion, the diagnostic tests, e.g. nucleic acid hybridization assays or immunoassays, may test for one or more of the retinal pigment epithelial protective proteins. Alternatively, they may consist of panel tests which test for both the retinal pigment epithelial protective proteins or retinal pigment epithelial protective nucleotide sequences, in combination with other proteins or nucleic acid sequences. The antibody compositions may consist of antibodies specific to a retinal pigment epithelial protective protein. The hybridization assays are preferably run at moderate to stringent conditions. The immunoassays are preferably conducted under conditions of reduced non-specific binding. Thus, the test kits and methods using these compositions are varied accordingly.

VI. Uses of Retinal Pigment Epithelial Protective Protein

According to another aspect of the present invention, there is provided a method of treating diseases associated with tissue damage due to oxygen metabolite production, comprising the steps of, first, providing a sample of tissue with damage due to oxygen metabolite production from a patient; and next, administering retinal pigment epithelial protective protein, biologically active variants or immunogenic fragments to the tissue such that the oxygen metabolite production is substantially inhibited and the patient is treated. The oxygen metabolites can be superoxide, nitric oxide, peroxide, hydrogen peroxide, hydroxyl radicals, peroxynitrite or any oxygen metabolite by-products.

In a preferred embodiment, the disease or condition are diseases can be selected from the group consisting of intraocular inflammation, uveitis, macular degeneration of the eye, retinal degeneration of the eye, secondary glaucoma, cataracts, optic nerve inflammation, corneal inflammation, scleral inflammation, stroke, arthritis, atherosclerosis (which can develop from toxic effects of oxygen metabolites) and any disease having inflammatory conditions where oxygen metabolites are involved in tissue damage.

In accordance with the present invention, RPP can be unique in function of suppressing inflammatory cells associated with tissue damage related to inflammation cause by the superoxide production. RPP can offer an approach in the treatment of inflammatory conditions involving the eye for example, macular degeneration, and other organs in the body. Furthermore, RPP can be utilized in gene therapy for the treatment of chronic inflammations using methods described herein.

In yet another aspect of this invention, RPP was injected intraocularly in experimental uveitis and the in vivo anti-inflammatory effects were examined. Specifically, RPP could lessen the level of superoxide production and superoxide-mediated inflammatory events in uveitis.

In accordance with another aspect of this invention, RPP is not limited to suppressing neutrophil oxygen metabolite generation associated with tissue inflammation, by the methods disclosed herein, but also, neutrophil macrophage oxygen metabolite generation.

The following examples are intended to illustrate but not limit the invention. While they are typical of those that might be used, other procedures known to those skilled in the art may alternatively be used.

Experimental Details

The following Examples below illustrate one important embodiment of the method according to the present invention.

EXAMPLES

Example 1

Characterization of the Suppressive Factor

Materials and Methods

Cell Culture and Characterization

All animals used for the cell cultures were maintained and treated in accordance with the ARVO Resolution on the Use of Animals in Research. Rat RPE cells were obtained by the method of McLaren et al. (1993) using Long Evans rats that were less than 15 days old. Collagenase/hyaluronidase and trypsin were used to digest extracellular matrix materials to free RPE. At the end of the digestion period, the eyes were opened by a circumferential incision just posterior to the ora serrata and the anterior segment and vitreous were removed. Under a dissecting microscope, retina was gently lifted off the eye cup. The RPE sheets were found largely attached to the retina and these were peeled off from the retina. Extreme care was taken to collect RPE in sheets and select only those sheets that were free of contamination by other cell types. No effort was made to collect maximal amounts of RPE cells. The pooled RPE sheets were trypsinized to obtain single cell suspensions and then plated in 25 cm² tissue culture flasks in RPE medium consisting of Eagle's minimal essential medium (MEM) (Gibco, Grand Island, N.Y.), 10% fetal bovine serum (Atlanta Biologicals, Norcross, Ga.) and antibiotics (penicillin at 100 units/ml, streptomycin at 100 μg/ml; Gibco). Only primary rat RPE cultures were used in this study.

Rabbit RPE cell cultures were obtained from pigmented rabbits (Irish Farm, Norco, Calif.) by the method of Flood, et al., *Invest. Opthalmol. Vis. Sci,* 19, 1309–20, 1980, with slight modification. Briefly, the freshly enucleated eyes were immediately submerged in the RPE medium. The globes were opened and cornea, lens, and vitreous humor were removed by a circumferential cut just posterior to the ora serrata. The neural retina was carefully washed out by the RPE medium. The eye cups were washed with Hank's balanced salt solution (HBSS), and were digested with 0.012% trypsin in 0.005% EDTA (Gibco) for 1 hr at 37° C. The trypsinization was stopped by adding excess RPE medium. The dissociated RPE cells were carefully washed out, without disturbing the underlying choroid. The RPE cells were first cultured in 12-well plates to near confluence with the RPE medium, and then were passed to 25 cm² flasks.

Rabbit skin fibroblasts (FB) from pigmented rabbits were obtained according to the method of Sotozono et al. (1994). The abdominal skin was first excised, sheared and cut into 1×2 cm pieces. These skin flaps were washed twice with $Ca^{++}$- and $Mg^{++}$-free phosphate-buffered saline, cut into small pieces and placed into 6-well plates. The culture medium was Dulbecco's modified Eagle's medium (DMEM; JRH Biosciences, Lenexa, Kans.), 15% fetal bovine serum and 1% penicillin/streptomycin solution. After 2 weeks, the cells were subcultured into 25 cm² flasks.

The corneal epithelial cell (CE) cultures were obtained by the procedure of Johnson-Muller and Gross, *Proc. Natl. Acad Sci. U.S.A.,* 75, 4417–21, 1978. Corneas were excised by cutting around the corneal periphery just inside the limbus, and then were incubated with 0.25% trypsin (Gibco) in $Ca^{++}$- and $Mg^{++}$-free HBSS for 12 hr at 4° C. After the incubation, the epithelium was gently pushed from the stromal surface with a blade. The isolated epithelial cells and cell clumps were collected by centrifugation and were cultured using the same medium used for the FB. For all the rabbit cell cultures, passages 1 and 2 were used for the study.

For establishing the purity of rat RPE cells, primary rat RPE cells were plated on 8-well chamber slides (Lab-Tek) and grown to near confluence. For detecting cytokeratin, the RPE cells were fixed in phosphate-buffered 4% paraformaldehyde, and blocked for 20 min with 2% goat serum and 2% bovine serum albumin (BSA) in phosphate buffered saline (PBS) before reacting with a 1:100 dilution of rabbit anti-human keratin (Dako Corp; Santa Barbara, Calif.) overnight at 4° C. Bound antibody was detected by incubating with a 1:200 dilution of biotinylated goat anti-rabbit IgG (Dako Corp.). Visualization was carried out first by reacting with an avidin-biotin complex (Vector Labs., Burlingame, Calif.) and then with a substrate, 3-amino-9-ethyl carbazole (Sigma, St. Louis, Mo.). Negative controls were incubated with PBS in place of primary antibody. For detecting cellular retinaldehyde binding protein (CRALBP), the rat RPE cells were similarly processed, reacted with a rabbit anti-bovine CRALBP (obtained by the methods found in Bunt-Milam, A.H. and Saari, J.C., *Gen. Cell Bio.,* 90, 703–12, 1983, herein incorporated by reference in its entirety). The secondary antibody used was the same as that in the detection of cytokeratin. For the immunoperoxidase detection of GFAP, rat RPE cells and rat astrocytes (positive control) were also fixed in 4% paraformaldehyde, and then were reacted for 30 min at 4° C. with a 1:300 dilution of rabbit anti-bovine GFAP (Dako Corp). The secondary antibody used was the same as that in the detection of cytokeratin. The rabbit RPE cells were characterized by immunoperoxidase detection of cytokeratin. The rabbit RPE cells were plated, fixed and blocked as rat RPE cells. The culture slides were then incubated with a 1:100 dilution of a mouse monoclonal antibody against bovine epidermal keratins (anti-cytokeratin 8.13, Sigma) overnight at room temperature. The secondary antibody used was biotinylated goat anti-mouse IgG diluted 1:200; visualization was with avidin-biotin complex and 3-amino-9-ethyl-carbazole.

PMN Superoxide Production in the Presence and Absence of RPE Cells, FB and CE Cells Rabbit and rat peritoneal neutrophils were collected according to the published procedure (McCarron et al., *Methods Enzymol.,* 108, 274–84, 1984. All PMN's used for the study contained over 95% PMN's as determined by Wright-Giemsa staining; there was no red blood cell contamination, and the viability of the cells was generally greater than 98%.

Generation of superoxide was measured by the SOD-inhibited reduction of cytochrome C. Basic assay procedures were performed as follows: two tubes of neutrophil suspension ($10^5$ to $10^6$ cells) in HBSS, one with 10 μl of SOD (3 mg/ml, Sigma) and the other with 10 μl of water, were incubated for 2 min at 37° C. before adding 50 μl of cytochrome C (30 mg/ml, Sigma) and phorbol myristate acetate (PMA) or N-formyl-methionylleucyl-phenylalanine (fMLP). The final concentrations of cytochrome C, PMA, and fMLP in a total of 1.5 ml of incubation mixture were 80 μM, 1.6 μM, and 0.5 μM, respectively. Optimum concentration of PMA and fMLP for PMN superoxide production have been reported previously. The mixture was then incubated at 37° C. for the desired length of time. The reduced cytochrome C was measured in a double-beam spectrophotometer (UV-160, Shimadzu, Kyoto, Japan), scanning between 570 and 530 nm (with maximum at 550 nm), using SOD-containing sample as the reference. The amount of superoxide produced was calculated by the molar extinction coefficient, 21,000 $M^{-1}$ $cm^{-1}$. In this procedure, although the reoxidation of cytochrome C has been reported to be negligible at neutral pH (Markert et al., *Methods Enzymol.,* 105, 358–65, 1984), the extent of reoxidation in the present system was nevertheless checked by adding 10 units/ml of catalase (Sigma).

A typical assay of superoxide generation in the presence of RPE cells, FB and CE cells contained the following three types of tubes: 1) PMN's with 10 μl of SOD; 2) PMN's with 10 μl of water, and 3) PMN's, 10 μl of water and other cells, including RPE (rat or rabbit cells), FB or CE. Cytochrome C was added to all 3 tubes along with either PMA or fMLP. The culture supernatants from these cells were also used for the assay. For collecting RPE supernatants, the adherent cells in the 25 cm² culture flasks were washed 6 times with HBSS before incubating with 2 ml of HBSS at 37° C. for 30 min. Alternatively, RPE cells were cultured in a serum-free medium for at least 24 hr before the supernatants were collected. The cultured supernatants from FB and CE cells were also collected by the same procedure. Sodium dodecyl sulfate-polyacrylamide gel electrophoresis (SDS-PAGE)

was routinely performed on RPE supernatant preparations to assure the absence of the intense BSA band, a major protein in the serum used for the tissue culture. Gel electrophoresis was carried out using 7.5% polyacrylamide gel and visualizing with a Bio-Rad silver staining kit (Bio-Rad, Hercules, Calif.). The cell numbers of PMN's, RPE cells, FB and CE cells used are indicated in the figure legends. Control runs with PMN's only were included for each set of experiments. For superoxide assays in each experiment, 2 to 3 replicate tubes were used and the same experiment was repeated at least 3 times.

To determine the relationship between the concentration of rabbit RPE supernatant proteins and the rabbit PMN superoxide generation, a serial dilution of proteins was made and tested for superoxide inhibitory activity. The concentration range of RPE supernatant proteins tested was from 0.625 µg/ml to 6.91 µg/ml. The amount of proteins in the supernatants was determined by the Bio-Rad method (Bio-Rad Laboratories, Hercules, Calif.) using BSA as standard.

PMN Superoxide Production in the Presence and Absence of Noncultivated RPE

The noncultivated RPE from bovine eyes was tested for RPP activity. The neural retina and vitreous were removed from 10 fresh bovine eyes obtained directly from the local slaughter house. Two different tissue preparations were made: RPE attached to choroid and choroid only. The RPE was removed along with the choroid to preserve the structural integrity of the RPE. The presence or absence of RPE in the two respective choroidal preparations was confirmed by hematoxylin-eosin histologic staining. These two tissues were incubated with 10 ml of HBSS at 37° C. for 1 hr and 4 hr and centrifuged at 3000 rpm for 15 min. The supernatants containing 92 µg each of total proteins from both samples were tested for superoxide suppressive activity in fMLP activated PMN's. To assure that the suppressive activity was not from the SOD activity present in these tissues, the supernatant from RPE-choroid preparation (92 µg proteins) was incubated with enzymatic superoxide generating system, including 50 µl of hypoxanthine (0.26 mg/ml, Sigma), 20 µl of xanthine oxidase (1.6 units/ml, Sigma), 50 µl of catalase (3.6 mg/ml, Sigma), and 100 µl of cytochrome C (37 mg/ml).

Degradation of RPP with Thermolysin

Rabbit RPE supernatants, 0.6 ml each obtained from $1.7 \times 10^5$ RPE cells, were incubated with either 10 or 50 µg/ml of thermolysin (43 units/mg; Sigma) for 15 min at 37° C. Following incubation, the reaction mixture was heated to 95° C. for 10 min to destroy excess thermolysin (Heinrikson, 1977) before it was subjected to assay for fMLP-stimulated PMN superoxide generation.

Effect of Cycloheximide on the Activity of RPP

Adherent rabbit RPE cells in 25 cm² culture flasks (average number of cells, $1.9 \times 10^5$ per flask) were incubated with either 10 or 50 µg/ml of cycloheximide (98% pure; Sigma) in 2 ml of HBSS at 37° C. for 2 hr. At the end of incubation, the viability of RPE cells was checked by trypan blue exclusion test. Exactly 1 ml each of supernatant was used for the subsequent assay of fMLP-stimulated PMN superoxide generation.

PMN Superoxide Production in the Presence of Transforming Growth Factor-,β (TGF-β) or Transferrin (Tf)

Two sets of experiments were performed to evaluate the effect of TGF-β on rabbit PMN superoxide generation. In the first set, rabbit PMN's ($9.6 \times 10^5$) were incubated with either 200 or 400 pM of TGF-β (purity>97%, from porcine platelets; R and D systems, Minneapolis, Minn.) (Brandes et al., 1991) for 1 hr. In the second set, 200 pM TGF-β was incubated with rabbit PMN's ($9.6 \times 10^5$) for 2 hr before stimulation with fMLP.

To evaluate the effect of Tf in rabbit PMN superoxide generation, 4 categories of experiment were set up to include the following: 1) 7 µg/ml of Tf (98% pure, human apo-Tf; Sigma); 2) 7 µg/ml iron-saturated Tf; 3) 700 µg/ml apo-Tf; 4) 700 µg/ml iron-saturated Tf. In both TGF-β and Tf experiments, two types of control runs, one with rabbit PMN's only and the other with PMN's+rabbit RPP, were also included. The fMLP-stimulated superoxide production was determined as described earlier.

Interaction of RPP with Superoxide Generated by Hypoxanthine and Xanthine Oxidase To test the possible SOD activity contained in RPP, total rabbit RPE supernatant (>10 kDa) as well as fractionated supernatant were used. Size fractionation was carried out using membrane ultrafiltration (Filtron, Northborough, Mass.) to separate into molecular weight (MWt) fractions of 10–50, 50–300, and >300 kDa. Following the separation, each fraction was reconstituted to 2 ml and the same volume from each fraction was used for the assay. To a mixture containing 1.265 ml of either HBSS or RPE supernatant, the following were added: 50 µl of catalase (3.6 mg/ml; Sigma), 100 µl of cytochrome C (37 mg/ml), 50 µl of hypoxanthine (0.26 mg/ml, Sigma), and 20 µl of xanthine oxidase (1.6 units/ml). Exactly 15 µl of SOD (3 mg/ml, Sigma) was added to the reference tube and 15 µl of water was added to the other tubes. The mixture was then incubated for 30 min and the quantity of superoxide produced was measured as described for PMN-generated superoxide. The level of superoxide generated in this system was similar to that released by PMN's. In addition, the supernatant proteins were incubated (1:1) with polyclonal rabbit anti-SOD antibody for 1 hr, centrifuged and the supernatant was then used in place of untreated RPP for the assay. Two 10 µl SOD samples (3 mg/ml), with and without the treatment of SOD antibody, were used to evaluate the efficiency of precipitation by SOD antibody.

Results

Characterization of Rat and Rabbit RPE Cell Cultures

The purity of primary rat RPE culture was established rigorously using the three available antibodies (cytokeratin, CRALBP and GFAP) for the rat system (McLaren et al., Exp. Cell Res., 204, 311–20, 1993). All the epithelial cells in the primary culture stained positive for cytokeratin and CRALBP. These positive stains were present in the cytoplasm of the cells. No staining was seen in the control (FIG. 1). None of the rat RPE cultures showed positive staining for GFAP. Similar to the rat RPE cells, the rabbit RPE cells were positive for cytokeratin and the positive reaction was noted in 100% of the cells (FIG. 2). The control was negative.

Figure 3:
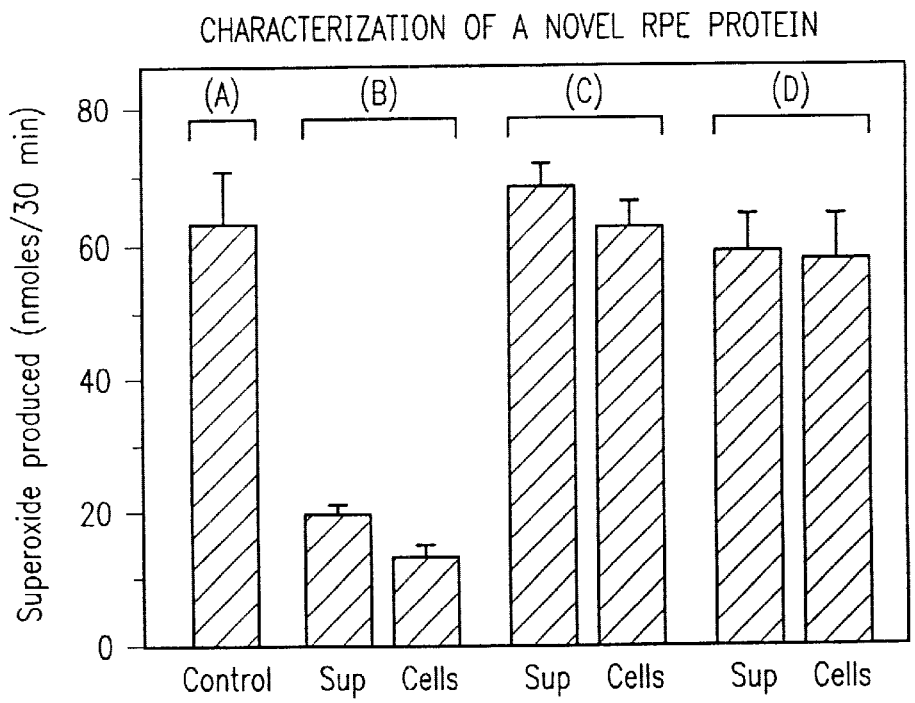
FIG. 3 graphically presents suppression of polymorphonuclear leukocyte (PMN) superoxide production by retinal pigment epithelial cells, skin FB and CE cells; rabbit peritoneal PMN's ($9.0 \times 10^5$) were incubated in the presence and absence of either rabbit RPE cells, rabbit skin FB or rabbit CE cells ($1.45 \times ^{105}$) for 30 min; results of (A) control with PMN's only; (B) PMN's+RPE cells or supernatants; (C) PMN's+skin FB (cells) or FB culture supernatants; (D) PMN's+CE cells or supernatants.
Figure 4:
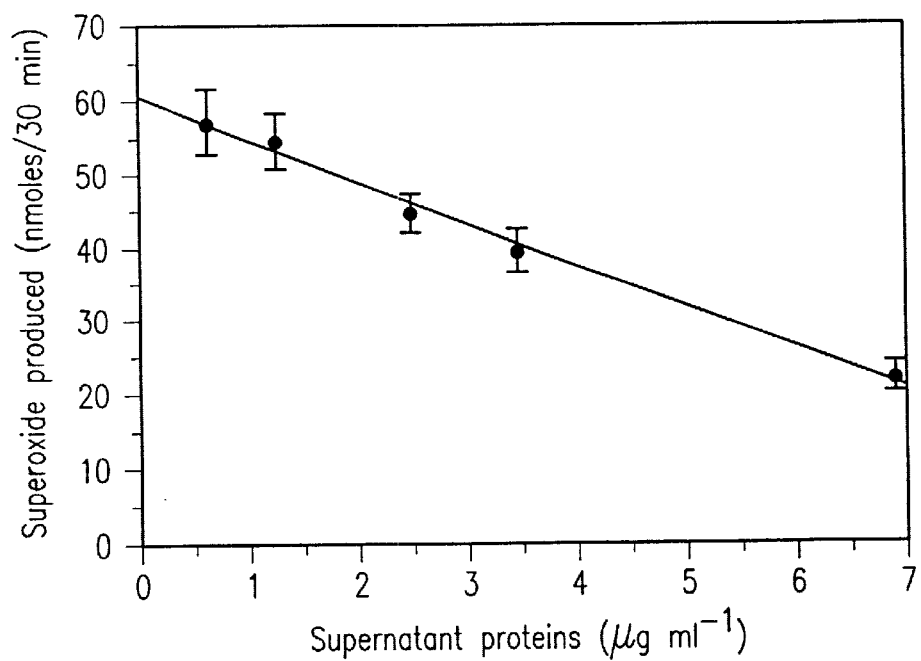
FIG. 4 graphically presents the relationship between concentration and suppressive activity of RPP.

Suppression of PMN Superoxide Generation by Cultured Rabbit and Rat RPE Cells and Supernatants Co-incubation of rabbit peritoneal PMN's with cultured rabbit RPE cells markedly inhibited the superoxide generation of PMN's stimulated with 0.5 µM fMLP. In the control runs with PMN's only, the amount of superoxide produced (50–60 nmoles/30 min for $8–9 \times 10^5$ cells) was comparable to the values reported by others. Following 30 min incubation, 80% inhibition was seen with cell ratios of PMN: RPE= 100:16. Under the same conditions, the co-incubation of PMN:FB and PMN:CE with the same cell ratios gave suppression of 3% and 9% on PMN superoxide generation respectively (FIG. 3). This trend in PMN superoxide inhibition also holds for these three culture supernatants. The culture supernatants were collected by incubating the same number of cells in each case with HBSS. The 30 min-incubation period was found to be sufficient to give substantial RPP activity for the assay. As indicated in FIG. 3, the supernatants collected from the same number of cells gave suppression of 69% and 8% for RPE and CE, respectively and an increase of 7% for FB. In the case of RPE, the inhibition appears to be more effective in the presence of cells than with the culture supernatant alone. The two-trailed Student's "t" test performed on the paired runs, RPE cells and RPE supernatants (FIG. 3B), indicated the p value to be <0.01. In this assay, the nonstimulated rabbit PMN's showed superoxide production of 0.6 nmole/30 min, and rabbit RPE cells alone with fMLP stimulation produced no detectable amount of superoxide. The inhibitory effect of RPE supernatants was also found to be concentration-dependent. When the supernatant proteins were increased from 0.625 $\mu$g/ml to 6.91 $\mu$g/ml, the PMN superoxide production was found to decrease from 57.2 nmoles to 22.4 nmoles, giving percentages of suppression from 10.0% to 64.7%. In the concentration range tested, the decrease in PMN superoxide generation was also found to be strictly proportional to the quantity of supernatant proteins present so that a good linear correlation (Y=60.166–5.5955X) was obtained (FIG. 4).

Figure 5:
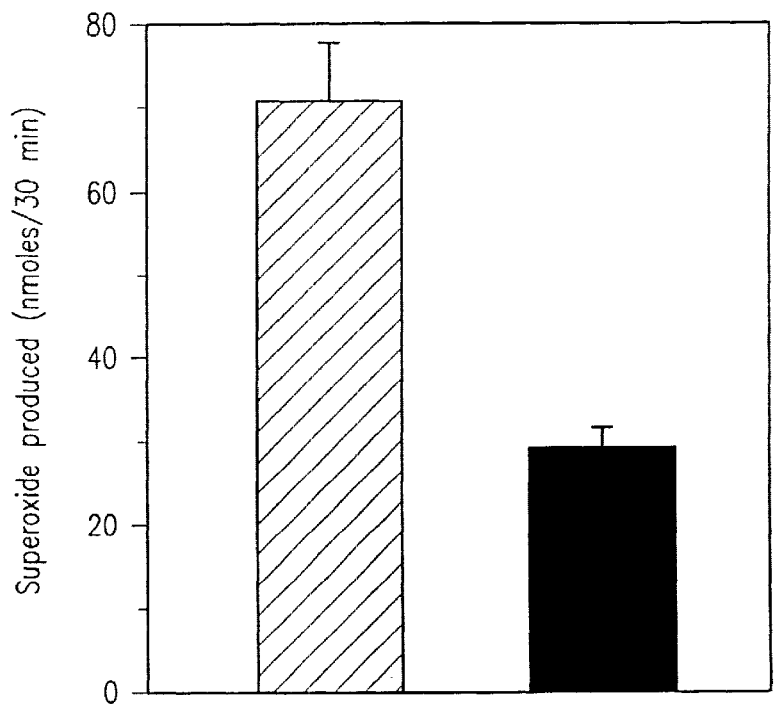
FIG. 5 graphically presents suppression of PMA-stimulated PMN superoxide production.

Activation of rabbit peritoneal PMN's with 1.6 $\mu$M PMA in the presence of rabbit RPE supernatants also produced a substantial suppression of PMN superoxide generation (FIG. 5). The RPE supernatants were collected from 0.75×10$^5$ RPE cells and this amounted to a cell ratio of PMN:RPE=100:9.9.

Figure 6:
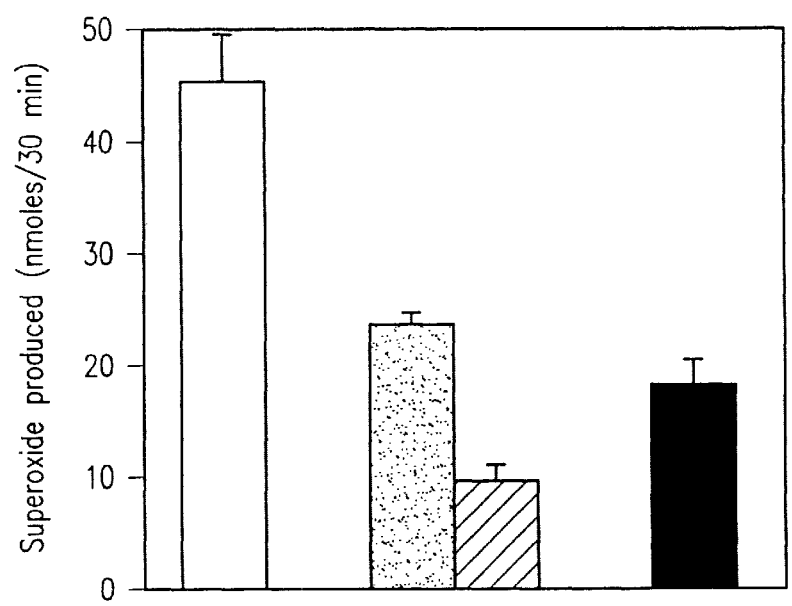
FIG. 6 graphically presents inhibition of rat PMN superoxide production by primary culture of rat RPE and rat RPE supernatant.

When rat peritoneal PMN's were stimulated with 1.6 $\mu$M of PMA, the presence of rat RPE cells also suppressed the PMN superoxide production (FIG. 6). In two runs with different cell ratios, namely PMN:RPE=100:3.5 and PMN:RPE=100:8.7, the suppressive effects generated appeared to be dependent on RPE cell numbers; the suppressions generated were 50% and 79% respectively. As in the case of rabbit RPE, the inclusion of rat RPE supernatant in the coincubation also produced a suppressive effect of 61%.

Suppression of PMN Superoxide Production by Noncultivated Intact RPE

Figure 7:
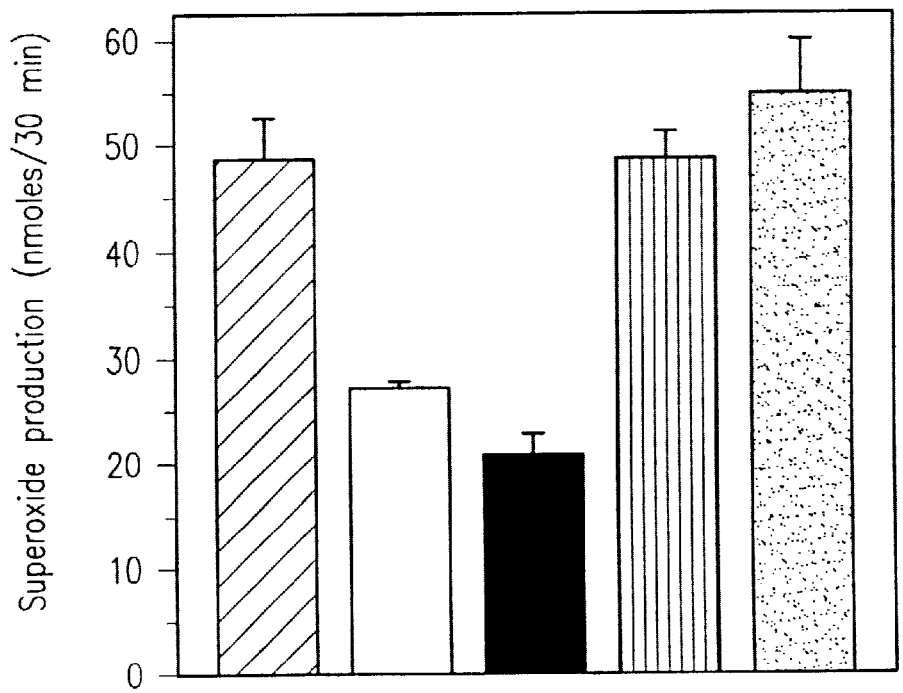
FIG. 7 graphically presents RPP activity in noncultivated intact RPE.

The noncultivated RPE isolated from the fresh bovine eyes also shows the suppression of PMN superoxide generation. The organ culture supernatants collected from RPE-choroid following 1 hr incubation with HBSS gave 44% suppression in PMN superoxide generation, whereas the supernatants collected after 4 hr incubation in HBSS gave 56% suppression. Under the same conditions, the supernatants collected by incubating the choroid alone in HBSS for 1 hr and 4 hr gave 0% suppression and 14% increase, respectively (FIG. 7). In order to assure that the suppression seen in the RPE-choroids was not due to the SOD activity contained in this preparation, the supernatants from intact bovine RPE-choroid were reacted with 67.8 nmoles of chemically generated superoxide (using hypoxanthine and xanthine oxidase), only 2% suppression in superoxide production was found in this system.

Characterization of the Inhibitory Factor, RPP

Initially, to confirm the proteinaceous nature of the inhibitory factor, the rabbit RPE supernatant was reacted with thermolysin, and the resultant cleavage products were tested for the activity. Typically, thermolysin, a neutral metalloendopeptidase, is known to cleave polypeptide backbones extensively and nonspecifically. It was found that 10 $\mu$g/ml of thermolysin incubated at 37° C., 15 min was sufficient to degrade the RPP totally so that no activity was detected. The RPP was also found to be heat labile: the activity was preserved following heating at 95° C. for 7 min, but 66% of the activity was lost after heating at 95° C. for 15 min, as indicated by the assays for PMN superoxide generation.

Figure 8:
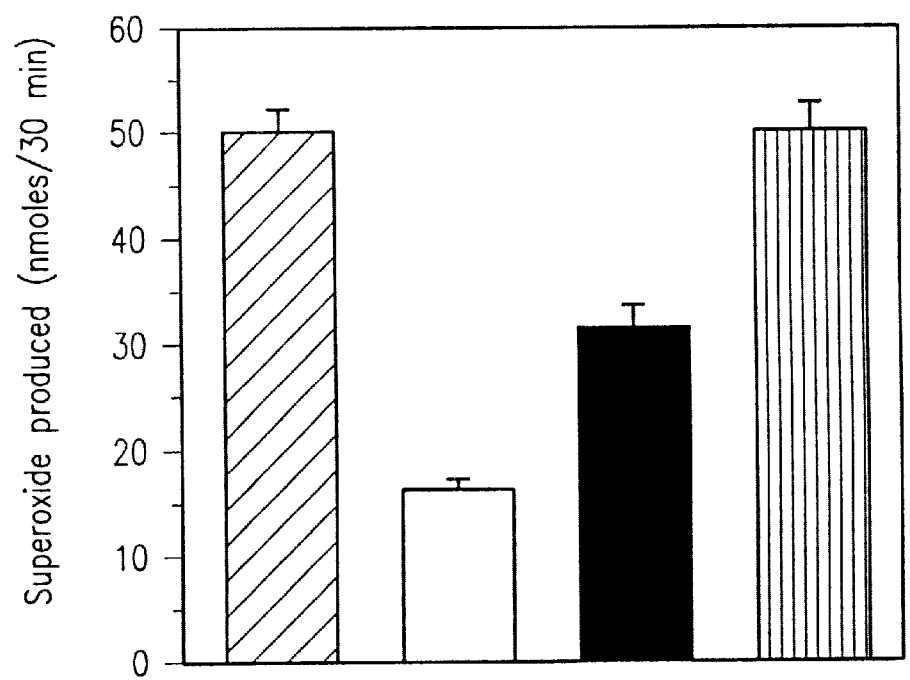
FIG. 8 graphically presents the effects of cycloheximide on RPP inhibitory activity.

To confirm the biosynthetic nature of RPP within RPE cells, the RPE cells were pretreated with cycloheximide before assaying for the activity. An optimum concentration range from about 5 to about 50 $\mu$g/ml of cycloheximide was chosen for this treatment to maintain both the viability of RPE cells and the normal respiratory burst of the PMN's following treatment. When adherent rabbit RPE cells were incubated with 10 $\mu$g/ml cycloheximide for 2 hr at 37° C. prior to the assay, the suppression of the supernatant was only 37% as compared with 67% for the untreated RPE supernatants (FIG. 8). Increased concentration of cycloheximide (50 $\mu$g/ml) gave suppression of 24% as compared with 67% for the RPP with full activity; but did not abolish the RPP activity totally. The incubation with either 10 or 50 $\mu$g/ml of cycloheximide up to 4 hr was not cytotoxic to either RPE or PMN cells, since cell viability for both remained equal to or larger than 95% as determined by trypan blue exclusion. Following cycloheximide treatment, the PMN respiratory burst was also found to unaffected as shown in FIG. 8.

To exclude the possibility that the decrease in superoxide production by PMN's is due to the cytotoxicity of RPP, the cell count and viability of the PMN's were determined following coincubation of rabbit PMN's with rabbit RPE cells or supernatants. As shown in Table 1, the RPP, in the form of either intact RPE cells or supernatants, is not cytotoxic to PMN's following 30 min coincubation. In the presence of RPP, there was approximately a 20% increase in the viability of PMN's and there was 4 to 5 times more intact PMN's which were not subjected to the respiratory burst-related destruction. In the absence of RPP, a substantial number of PMN's were found to disintegrate at the end of 30 min incubation. The RPE cells are slightly more effective than the supernatants in delivering this protective effect.

TABLE I

Effect of rabbit RPE cells and supernatant on rabbit PMN cell count and viability*†

| Incubation mixture | Cell count (× 10$^5$ cells ml$^{-1}$) | Viability (%) |
|---|---|---|
| PMN only | 1.13 ± 0.18 | 66 ± 7 |
| PMN + RPE supernatant‡ | 4.43 ± 0.38 | 86 ± 4 |
| PMN + RPE cells‡ | 5.49 ± 0.43 | 89 ± 5 |

*The PMN count and viability at 0 min incubation were 5.97 ± 0.50 × 10$^5$ cells ml$^{-1}$ and 97 ± 3%, respectively. Incubation was carried out for 30 min.
†The results were expressed as means ±S.D. (n = 3).
‡At 0 min, PMN's and RPE cells used were 5.97 ± 0.50 × 10$^5$ and 1.01 ± 0.15 × 10$^5$ respectively. RPE supernatant was collected from the same number of RPE cells.

Figure 9:
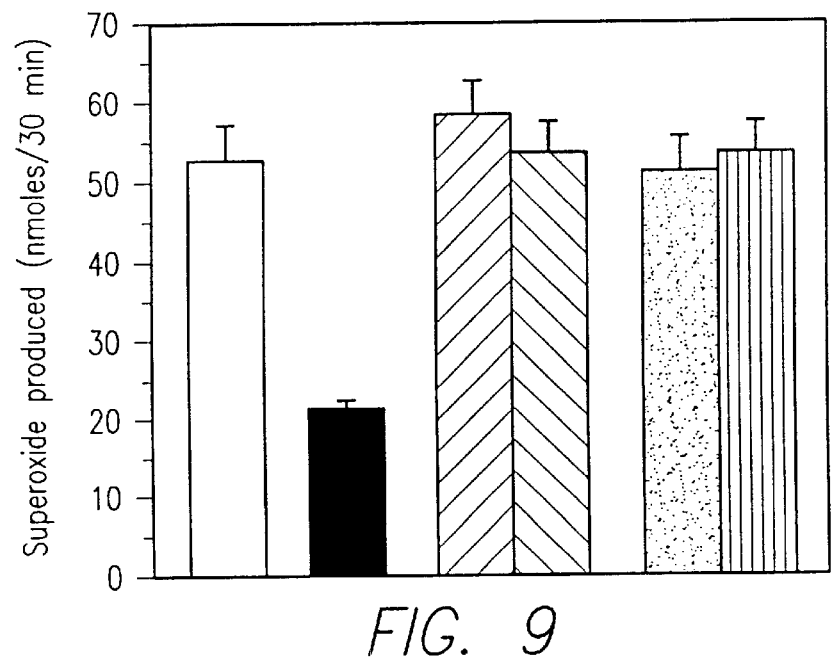
FIG. 9 graphically presents the effect of TGF-β and Tf on PMN superoxide production.

To attempt to identify the RPP, we first excluded the possibility of contamination by two known factors, TGF-$\beta$ and Tf, which are potential modulators of neutrophil. Both TGF-$\beta$ and Tf were tested for their effect on the PMN superoxide production under the same conditions used for the assay of RPP activity. Incubation of rabbit PMN's with 200 pM or 400 pM TGF-$\beta$ for 1 hr gave superoxide production of 111% and 102% respectively as compared with 100% production by PMN's in the absence of TGF-$\beta$ (FIG. 9). These concentrations have been indicated to be suitable for testing the biological activity of TGF-$\beta$. The apo- and iron-saturated human Tf with the concentration of 7 $\mu$g/ml, gave PMN superoxide production of 98% and 102% respectively as compared with 100% for PMN's without Tf (FIG. 9). With 700 µg/ml of either apo- or ironsaturated Tf, the PMN superoxide production was 145% and 172%, respectively. Under the same conditions, the RPE supernatants containing 7.0 µg/ml of total proteins gave PMN superoxide production of 40% as compared with 100% for the PMN only control (FIG. 9).

Figure 10:
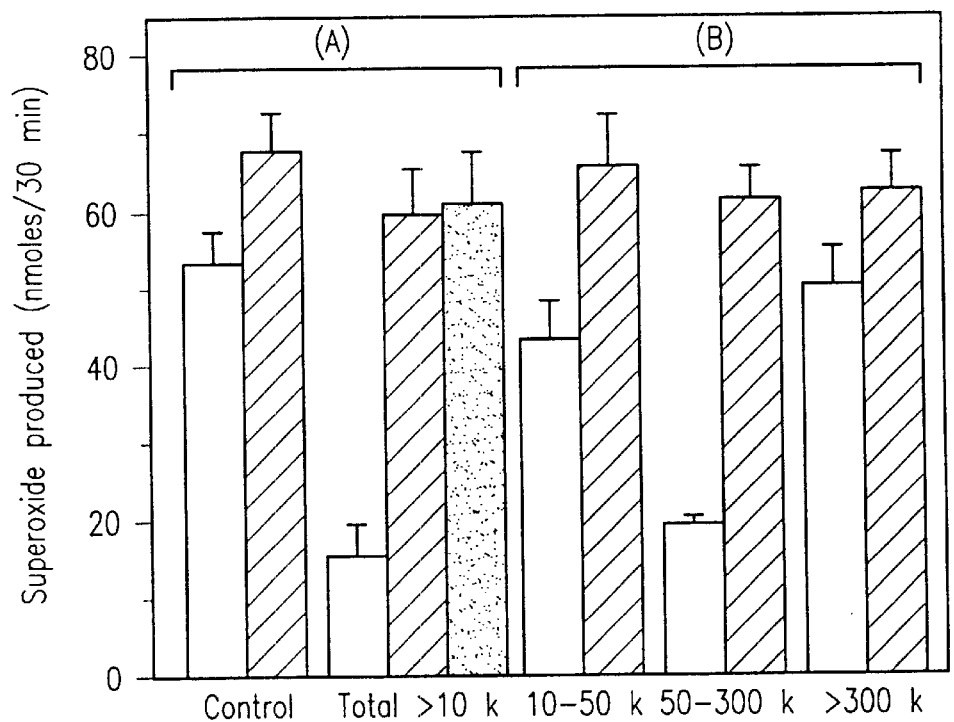
FIG. 10 graphically presents the effect of RPP on PMN- and enzymatic-superoxide generation.

To exclude the possibility that the RPP activity was derived from SOD or SOD-like compounds, experiments were conducted to test the effect of RPP in a PMN-free system, in which the superoxide was enzymatically generated. In these experiments, when the total rabbit RPE supernatants were reacted with 67.5 nmoles of enzymatically generated superoxide, the production of superoxide was 88% (59.4 nmoles) as compared with 100% for the control without RPP (FIG. 10A). In the same experiment, RPP reduced the rabbit PMN-derived superoxide production (53.2 nmoles ) to 15.8 nmoles (FIG. 10A). In the second set of assays, in an attempt to estimate the approximate MWt range of RPP, the total rabbit RPE supernatant proteins were separated into 3 fractions: 10–50, 50–300, and >300 kDa and their effect in both systems, hypoxanthine/xanthine oxidase and PMN, was assessed. The enzymatic superoxide production was found to be 97%, 93% and 92% of the control; whereas, in PMN system, the superoxide production was 82%, 36% and 95% for the fractions, 10–50, 50–300 and >300 kDa, respectively (FIG. 10B). Furthermore, to assure that the small extent of suppression seen in enzymatic superoxide generation is not due to the SOD-type scavenging, the total RPP were treated with anti-SOD antibody and the assays were repeated. The production of enzymatic superoxide in the presence of Sod antibody-treated RPP was ×90% (FIG. 10A). Neutralization efficiency of this antibody with the authentic SOD was found to be 91%.

Example 2

Purification and Microsequencing Analysis of Retinal Pigment Epithelial Protein

Materials and Methods

All animals used for the cell culture were maintained and treated in accordance with the ARVO Resolution on the Use of Animals in Research. The RPE cell cultures from pigmented rabbits (Irish Farms, Norco, Calif.) were obtained and characterized as described in detail in Example 1. The culture medium used was Eagle's minimal essential medium (MEM; Gibco, Grand Island, N.Y.), containing 10% fetal bovine serum (Atlanta Biologicals, Norcross, Ga.), 1% 200 mM glutamin and 1% penicillin/streptomycin (Gibco). All RPE cultures used were from either passage 2 or 3.

To obtain supernatant proteins from these cells, two different methods were used to assure the absence of tissue culture serum from the supernatants collected. The confluent RPE cells in the 25 cm$^2$ culture flasks were washed 6 times with Hank's balanced salt solution (HBSS) before incubating with 2 ml of HBSS for 4 hr to collect supernatant proteins. The quantity of supernatant proteins collected was found to increase steadily up to 4–5 hr incubation, and then to level off thereafter. At the end of 4-hr incubation, the RPE cells were not disrupted and were generally placed back into the RPE medium for reculturing. Alternatively, after the RPE cells reached confluency, they were cultured in a serum-free medium (MEM, glutamin and antibiotics) for at least 40 hr before the cells were washed and incubated in 2 ml of HBSS for 4 hr for supernatant collection. In these two preparations, the bovine serum albumin (BSA) band, a major protein in the serum, were found to be absent by the sodium dodecyl sulfate-polyacrylamide gel electrophoresis (SDS-PAGE) using 7.5% polyacryamide gel and visualizing with a Bio-Rad silver staining kit (Bio-Rad, Hercules, Calif.). The proteins were determined by the Bio-Rad method (BioRad) using BSA as standard.

For the assay of superoxide produced by PMN's in the presence of RPP, the superoxide dismutase (SOD)-inhibited reduction of cytochrome C was measured. The assay contained the following three types of tubes: 1) PMN's with 10 µl of SOD (3 mg/ml, Sigma, St. Louis, Mo); 2) PMN's with 10 µl of water; and 3) PMN's, 10 µl of water and RPP. Cytochrome C (final concentration, 80µM) and N-formyl-methionyl-leucyl-phenylalanine (fMLP, final concentration, 0.5 µM) were added to all tubes. The mixture was then incubated for 30 min at 37° C. and the reduced cytochrome C was measured in a double-beam spectrophotometer (UV-160, 1Shimadzu, Kyoto, Japan) using the SOD-containing sample as the reference. The molar extinction coefficient of 21,000 M$^{-1}$ cm$^{-1}$ as used to calculate the amount of superoxide produced.

Sodium Dodecyl Sulfate-Gel Electrophoresis

The SDS-PAGE was performed in minigel formats (Hoefer Scientific, SE 250, San Francisco, Calif.). The separating gel of either 7.5%, 10%, or 12% polyacrylamide was cast with a 4% stacking gel and the SDS-buffer system used was according to Laemmli (1970). The detection of the protein bands was carried out by silver staining (Bio-Rad), using the silver stain high range SDS-PAGE standard (Bio-Rad) as MWt marker.

Anion Exchange Chromatography on DEAE SEPHAROSE® CL-6B

Pooled RPE supernatant (1,900 ml in HBSS) was concentrated at 4° C. by ultrafiltration over a YM-10 membrane (cut-off, 10 kDa, Amicon, Lexington, Mass.) to about 70 ml, and was then dialyzed against 41 of 10 mM Tris-HCl (pH 7.6) for overnight. The dialyzed material was then loaded on an anion exchange column, 2.6×17 cm, packed with DEAE SEPHAROSE® CL-6B (Pharmacia, Piscataway, N.J.). The column was eluted with 200 ml of buffer A, 10 mM Tris-HCl (pH 7.8), before switching to a linear gradient of 0–1 M NaCl in buffer A (total gradient volume, 300 ml; flow rate, 48 ml/hr; and fraction size, 8 ml). The eluates were pooled into 6 fractions and were analyzed for the inhibitory activity, protein concentration and SDS-PAGE.

Anion Exchange-High Performance Liquid Chromatography (AE-HPLC) and Reversed Phase-High Performance Liquid Chromatography (RP-HPLC)

The fractions obtained from the initial large capacity anion exchange chromatography were further purified with AE-HPLC and RP-HPLC. In the microseparation AE-HPLC (Pharmacia's SMART system), an anion exchange column, MONO Q® 1.6/5 (column volume, 100 µl) was used. The elution conditions for the column were as follows: flow rate, 100 µl/min; fraction size, 100 µl; and detection at 280 nm. This system offers state-of-the-art micropurification capability with concomitant concentration. Buffer A was 10 mM Tris-HCl (pH 7.8) and buffer B was 1 M NaCl in buffer A. The elution was programmed to run buffer A for 40 min, followed by a gradient elution to reach 100% of buffer B in 50 min. The fractions collected were analyzed for inhibitory activity, protein concentration and SDS-PAGE.

The RP-HPLC system was assembled and the microcapillary column was packed at the Beckman Research Institute of the City of Hope (Duarte, Calif.). The instrument consists of a 20 cm fused silica column (inner diameter, 560 µm) packed with a 3 µm vydac C18 reversed phase support, an Applied Biosystems 140A solvent delivery system, a Shimadzu SPD-6A UV-VIS detector, and a Soltec 1241 recorder. Buffer A was 0.1% trifluoroacetic acid (TFA), and buffer B was 0.07% TFA in 90% acetonitrile. The gradient elution was from 2% to 90% buffer B in 90 min. The flow rate used was 20 µl/min, the detection was at 214 nm, and the fractions were collected manually according to the elution profile.

Microsequencing Analysis of RPP

Before performing microsequencing, the doublet on the purified RPP (see FIG. 1) was further separated by a preparative scale SDS-PAGE. Approximately 32 µg of either AE-HPLC- or RP-HPLC-purified RPP was loaded on the SDS-PAGE, using 8 lanes of 1.5 mm thickness minigel to separate the RPP doublet (FIG. 1). Following SDS-PAGE, the protein bands were electrotransferred to a polyvinylidene difluoride (PVDF) membrane (Millipore, Bedford, Mass.), using a mini trans-blot electrophoretic transfer cell (Bio-Rad) at constant 250 mA. The PVDF membrane-bound proteins were visualized with 0.1% Ponceau S in water (containing 10% methanol, 1% acetic acid, 1.5% trichloro-acetic acid, and 1.5% sulfosalicylic acid). The doublet protein bands were excised separately and subjected to automated Edman degradation for N-terminal sequence analysis using an Applied Biosystems gas phase sequencer 470A equipped with an on-line phenylthiohydantoin amino acid analyzer 120A from the same manufacturer (at Beckman Research Institute of the City of Hope). The resulting phenylthiohydantoin amino acid derivatives were identified by on-line RP-HPLC. The standard sequencing program 03RPTH was used.

"On membrane" trypsin internal digestion of RPP was performed. The membrane was first blocked for 30 min with 0.5 ml of 1% hydrogenated Triton X-100 (RTX-100) in methanol. The air-dried bands were cut in small pieces and placed in 50 µl of digestion buffer (containing 1% RTX-100 and 10% acetonitrile in 100 mM Tris-HCl, pH 8.0). Trypsin was added in the mole ratio of trypsin/substrate (1:10) and the reaction mixture was incubated at 37° C. for 24 hr. The trypsin digests were separated on a C18 vydac microcapillary column. The condition used for RP-HPLC has been described earlier in this section.

The selection of peptide fragments for the subsequent microsequencing was based on the analyses by SIMS which provided information on the homogeneity of the fraction as well as possible contamination of autodigested trypsin in that fraction. A 1-µl aliquot from all of the major fractions of trypsin digestion was subjected to analysis by SIMS. Mass spectra were recorded in the positive ion mode using a TSQ-700 triple sector quadrupole instrument (Finnigan-MAT, San Jose, Calif.) equipped with a Cs ion gun (Phrasor Scientific Inc., Duarte, Calif.). Scans were acquired every 7 sec in mass per charge ratio (m/z) from 400 to 4,000. All mass spectra were generated by averaging the scans containing the peak, and the masses were calculated using Finnigan MAT's BIOMASS data reduction software. The similarity search was performed through the E-mail service at the National Center for Biotechnology Information (National Library of Medicine, National Institute of Health, Bethesda, Md.) using the BLAST program.

Results

Purification of RPP

Figure 11A:
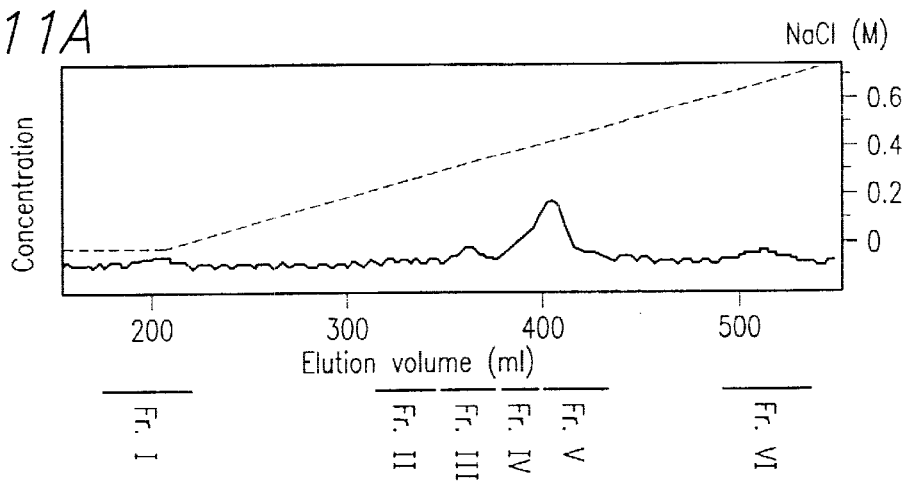
FIG. 11 illustrates anion-exchange chromatography of RPE supernatant proteins and superoxide inhibitory activity of chromatographic fractions; (A) DEAE SEPHAROSE® CL-6B column first eluted with buffer A, followed by a linear gradient of 0 to 1 NaCl in buffer A; (B) PMN superoxide production in the presence of Fr. I through Fr. VI.
Figure 11B:
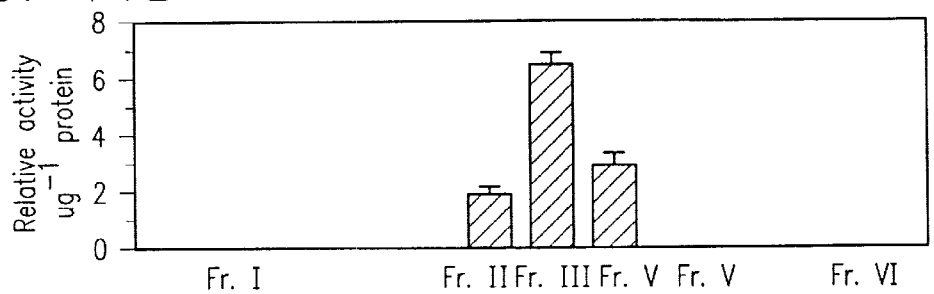

In the preceding Example 1, the fractionation of the total supernatant proteins indicated that the active component resided in the 50 to 300 kDa fraction. Gel filtration with Sephadex G-100 was subsequently attempted as a first step purification of RPP. However, the low volume capacity of this chromatography coupled with the necessity to concentrate the broad eluate peaks prompted us to change to anion exchange chromatography for initial purification. Anion exchange chromatography appeared to circumvent the difficulties encountered in gel filtration; the peaks obtained were sufficiently narrow to allow testing of activity without further concentration. In a typical run, a load of 3.08 mg of total RPE supernatant proteins onto DEAE SEPHAROSE® CL-6B column resulted in 6 pooled fractions (FIG. 11A). The total proteins in these fractions were as follows: Fraction (Fr) I, undetectable; Fr. II, 90 µg; Fr. III, 232 µg; Fr. IV, 825 µg; Fr. V, 1740 µg; and Fr. VI, undetectable. The inhibitory activity was found to be retained, with the activity residing predominantly in Fr. III and the front and tail ends of this peak extending into adjacent fractions (FIG. 11B). The quantities of superoxide produced per µg of protein from these three fractions were 39.5, 19.2 and 34.9 nmoles for Fr. II, III and IV respectively, as compared with 48.0 nmoles for the control with the PMN's only. Therefore, the suppression of superoxide production for these fractions were 18%, 60% and 27% respectively (FIG. 11B). The DEAE SEPHAROSE® CL-6B chromatography of total serum proteins from fetal bovine serum used in the tissue culture was also carried out. Under identical conditions, the serum proteins were found to give a different elution profile from that of RPE supernatant proteins; a major peak was found to center at the elution volume of 430 ml and no peak was found in the elution volume identical to that of the active peak (Fr. III), 375 ml.

Figure 12A:
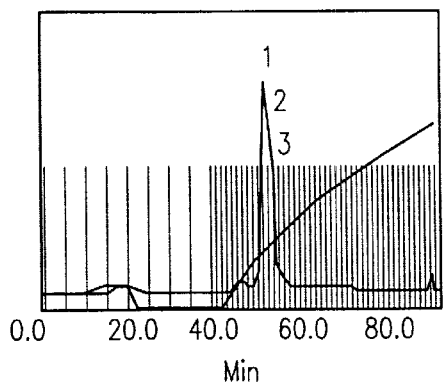
FIG. 12 illustrates anion-exchange HPLC of Fr. III and IV. from FIG. 11; (A) six runs from Fr. III and (B) three runs from Fr. IV; (C) the results from three chromatographic runs.
Figure 12B:
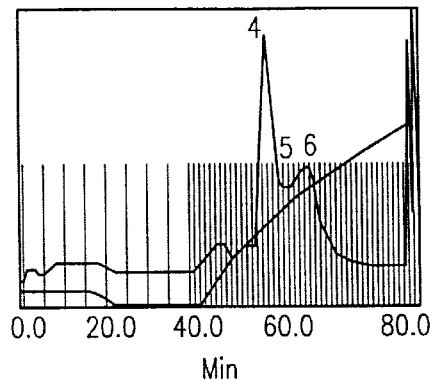
Figure 12C:
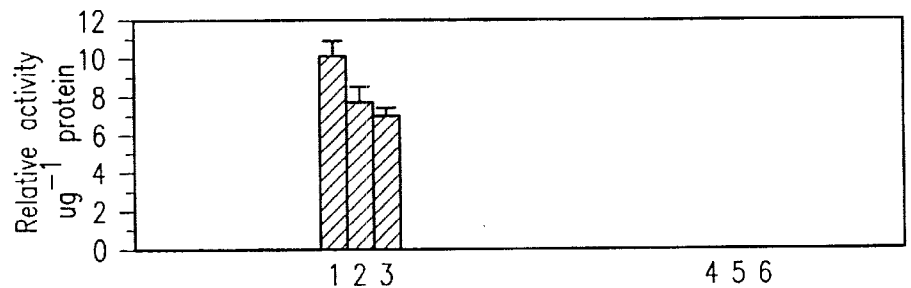
Figure 13:
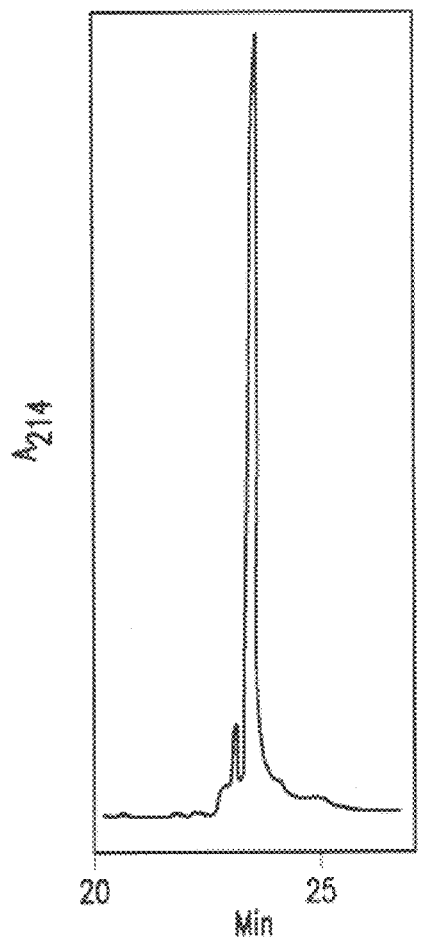
FIG. 13 illustrates reversed-phase HPLC of RPP.

The secondary phase of purification for the active Fr. III was carried out by a microseparation AE-HPLC (FIG. 12) and a RP-HPLC utilizing a microcapillary column (FIG. 13). In AE-HPLC, the re-chromatography of the active Fr. III gave only one major peak comprising three closely related peaks. These three peaks were not resolvable even with a slower gradient. The activity was retained in these three peaks to indicate that all of three fractions (1, 2 and 3 in FIG. 12A), derived originally from Fr. III (FIG. 11A), displayed activity. The PMN superoxide generation in the presence of fractions 1, 2 and 3 was 1.8, 13.2 and 15.5 nmoles/µg for fractions 1, 2 and 3, respectively, as compared with 45.5 nmoles for the control with PMN's only. These superoxide values also represent the suppressive activities of 96%, 71% and 66%, respectively, for the three fractions. The increase in biological activity per µg of protein of these AE-HPLC purified fractions was less than 4-fold as compared with that of crude RPP. A substantial activity could be lost during chromatographic manipulations. The peaks, 4, 5 and 6 in FIG. 12B, which were rechromatography of Fr. IV of FIG. 11A, were found to be totally inactive (FIG. 12C). In this chromatogram (FIG. 12B), however, there are minor components seen at the retention time of 52 min (the same retention time as the major peak in FIG. 12A), and these might to be responsible for the activity seen for Fr. IV (FIG. 11B). The active Fr. III (FIG. 11) was also re-chromatographed in RP-HPLC using microcapillary C18 vydac column. The chromatogram gave a sharp single peak, amounting to more than 90% of the total area. The biological activity of fractions from RP-HPLC (FIG. 13) was not tested, since the activity would not be retained by acetonitrile/TFA elution.

Sodium dodecyl sulfate-polyacrylamide gel electrophoresis with silver staining was used to assess the homogeneity of the fractions in each step of purification, using both 7.5% and 10% polyacrylamide. Under non-reducing conditions, the active Fr. III from DEAE SEPHAROSE® chromatography (FIG. 11A and B) showed one broad diffused band centered at 90 kDa. Under a reducing condition, total RPE soluble proteins displayed numerous bands in all the areas (FIG. 14, lane 4). The Fr. III (FIG. 11A) showed an intense doublet, with MWt close to 69 and 75 kDa as estimated by SDS-PAGE standard and the corresponding relative mobility values (FIG. 14, lane 3). In the total supernatant protein (FIG. 14, lane 4), there appears to be a low intensity band(s) corresponding to this mobility. In Fr. III, low intensity minor bands located above and below the major doublet were also visible. These minor bands, however, were excluded by the subsequent secondary purification, using either AE-HPLC or RP-HPLC. All of three major AE-HPLC fractions (1, 2 and 3 in FIG. 12A) and the major peak in RP-HPLC (FIG. 13) showed the intense 69/75 kDa doublet, with slightly different proportions of the two bands between individual fractions. Both fractions 1 and 2 (FIG. 12A) from AE-HPLC and the center fractions from RP-HPLC showed only the doublet, without any other minor contaminating bands (FIG. 14, lane 2). These fractions were used for the subsequent microsequencing analysis. From the microsequencing, these two bands were subsequently found to be the same proteins, differing only in minor structural modification.

Microsequencing Analysis of RPP

Figure 15A:
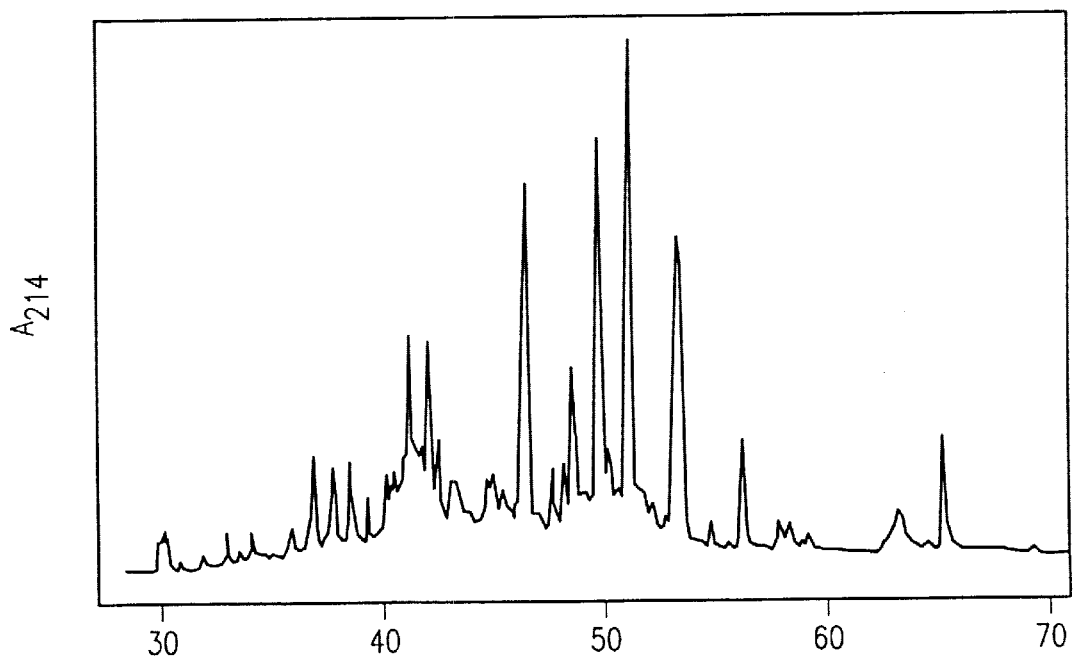
FIG. 15 illustrates tryptic digestion of RPP; (A) upper band digests; (B) lower band digests
Figure 15B:
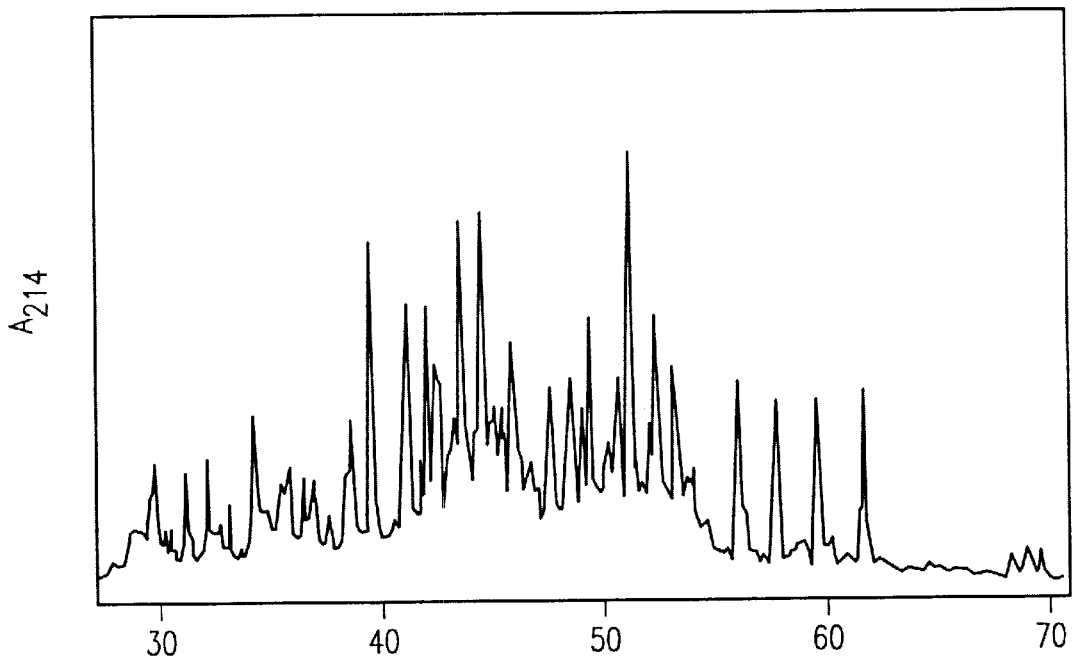
Figure 16A:
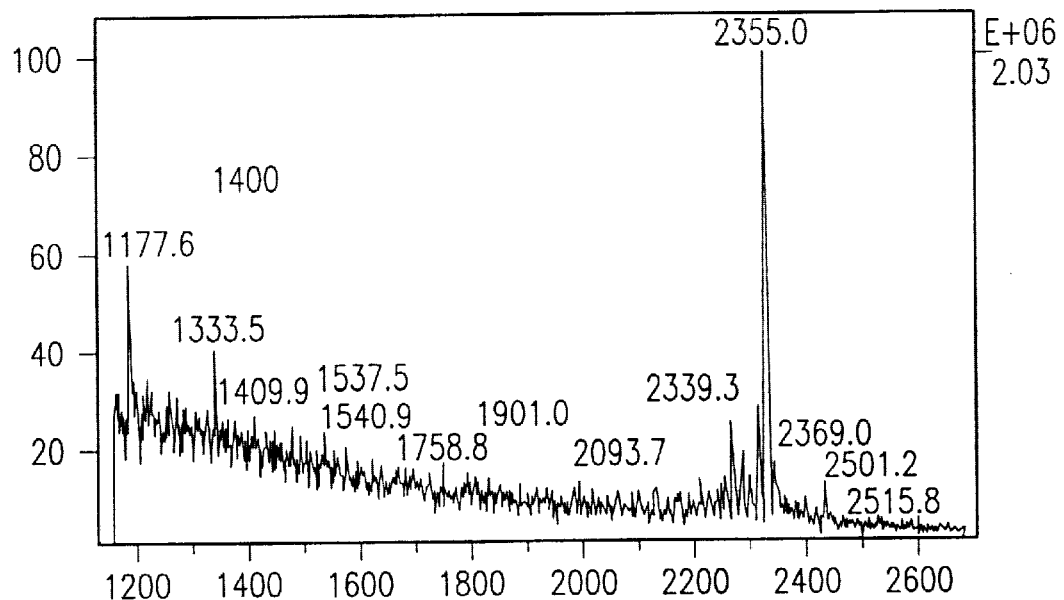
FIG. 16 illustrates secondary ionization mass spectrometry of tryptic digests of RPP; (A) tryptic digest, pdak No. 50 from RPP upper band (shown in FIG. 14); (B) tryptic digest, peak No. 59 from RPP lower band (shown in FIG. 14)
Figure 16B:
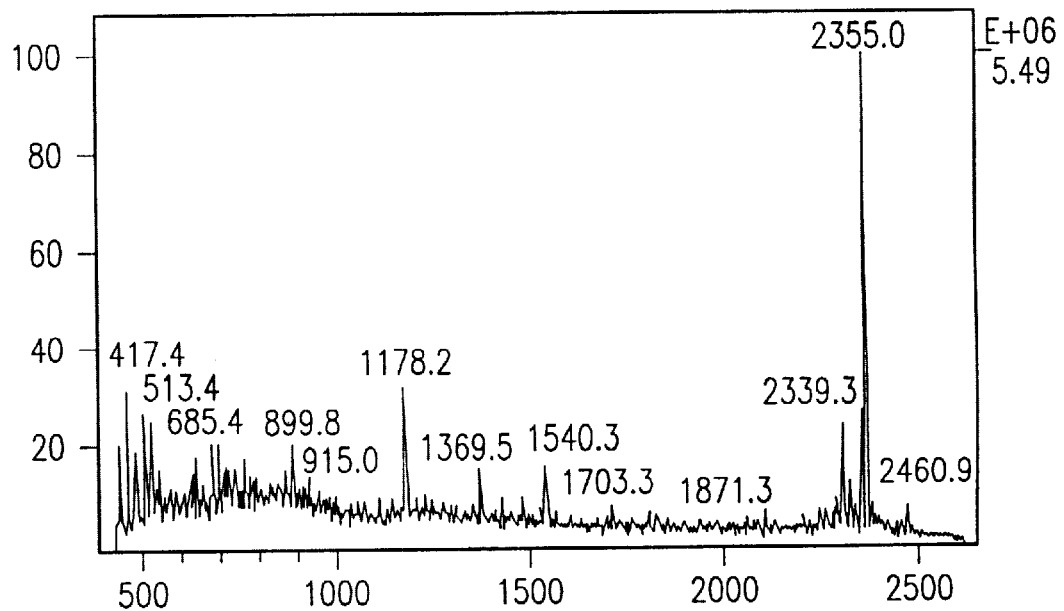

The approach taken for the amino acid sequence determination involves a combination of mass spectral analysis and sequential Edman degradation. The initial Edman degradation of the RPP doublet (FIG. 14) was unsuccessful, suggesting that the N-termini were blocked for both proteins. The separate tryptic digestion of upper and lower RPP bands resulted in 30 to 40 each of moderate- to high-intensity tryptic peptides. The typical RP-HPLC of the tryptic digests for these two proteins is shown in FIG. 15A and B. The SIMS analysis was then performed for each of the tryptic peptides shown in FIG. 15. This type of mass spectrometrical analysis collects the molecular ions without any fragmentation ions from the polypeptide backbone; thus the resulting spectra are relatively simple: only the molecular ions of the polypeptide are present. Therefore, the SIMS analysis gives the information on the homogeneity of each trypsin digest in FIG. 15A and B, and provides the basis for choosing appropriate peaks for subsequent sequencing analysis. Two examples of SIMS spectra for the fractions selected for the sequencing analysis, peak #50 from FIG. 15A and peak #59 from FIG. 15B, are shown in FIG. 16A and B, respectively.

The mass analyses from SIMS also indicated that the upper- and lower-band proteins (FIG. 14) are closely related structurally since the masses (MWts) of almost all of the tryptic peptides obtained are the same for both proteins. The SIMS analyses also indicated that a small proportion of the digested fragments matches those in the database for tryptic digests from transferrin (Tf) family proteins in their masses. For example, in one run of trypsin digestion of the lower band protein (FIG. 14), 13 major fragments were run through SIMS. Among these, two fragments matched the trypsin digests from bovine Tf, one matched human Tf, and two matched rabbit Tf. From tryptic digestions of both upper and lower bands, a total of 8 polypeptide sequences, ranging from 10 to 25 amino acids, were obtained (Table 2). A total of eight runs of tryptic digestions were carried out from both lower and upper bands and the peptides sequenced were indicated in Table 2. Most of the sequences appeared more than once in these analyses from different runs. As shown in Table 3, from the similarity search, three of the peptide sequences (peak #52, peak #27 and peak #34,) revealed some degree of homology with Tf from various species. The remaining five sequences are unique in that no related sequence was found in the database.

TABLE II

Partial amino acid sequences of trypsin-generated peptides from purified RPP

| Peptide | SEQ ID NO. | Amino acid sequence |
|---|---|---|
| Peak No. 50 | 1 | MGIELYGYYXXSALGEK |
| Peak No. 42 | 2 | NQ(N)KVQKQA(N)MHMQXYL |
| Peak No. 52 | 3 | (A)FSNNEADAVTLDGGLVYEAGLSPN |
| Peak No. 22 | 4 | FLVL(N)KTVVG |
| Peak No. 27 | 5 | GYLAVA(V)VISLGS |
| Peak No. 29 | 6 | S(A)ELNKFMGR |
| Peak No. 34 | 7 | ELVESGLVAFVSX(E)SXEXSSP |
| Peak No. 24 | 8 | GYLALPAFQSLGXXN |

Peptides from RPP were generated and subjected to amino acid sequence analyses as outlined under Experimental Procedures. Residues within parentheses indicate the most prominent identified amino acid in positions where more than one amino acid was identified. X denotes the cycle where no amino acid was identified.

TABLE III

Homology similarity of RPP to the known peptides in the database[a]

| Known protein | RPP peptide | | | | | | | |
|---|---|---|---|---|---|---|---|---|
| | No. 50 | No. 42 | No. 52 | No. 22 | No. 27 | No. 29 | No. 34 | No. 24 |
| Lactotransferrin | | | | | | | | |
| Human | —[b] | — | 69.6 | — | 64.1 | — | — | — |
| Bovine | — | — | 59.6 | — | 64.1 | — | — | — |
| Mouse | — | — | 47.4 | — | 56.1 | — | — | — |
| Serotransferrin | | | | | | | | |
| Horse | — | — | 76.6 | — | — | — | 53.0 | — |
| Pig | — | — | 71.9 | — | 64.1 | — | 46.1 | — |
| Rabbit | — | — | 70.2 | — | 60.9 | — | — | — |
| Human | — | — | 69.6 | — | 55.4 | — | 45.2 | — |
| Ovotransferrin | | | | | | | | |
| Chick | — | — | 71.3 | — | — | — | — | — |

[a]Data are expressed as percent match in sequence homology.
[b]No matched sequence was found in known proteins with similar molecular weight.

Example 3

Inhibition of Superoxide Generation in Experimental Uveitis by Retinal Pigment Epithelial Protein Materials and Methods Twelve pigmented rabbits (Irish Farms, Norco, Calif.), weighing 2 to 2.5 kg, were used in the study. The animals were maintained and treated in accordance with the ARVO Statement on the Use of Animals in Ophthalmic and Vision Research.

A crude preparation of RPP was obtained from rabbit RPE cultures according to a Experiment 1. Briefly, RPE cells obtained from pigmented rabbit eyes were cultured in Eagle's minimum essential medium (MEM; Gibco, Grand Island, N.Y.), supplemented with 10% fetal bovine serum (Atlanta Biologicals, Norcross, Ga.), 1 mM glutamine, 100 u/ml penicillin (Gibco) and 100 u/ml streptomycin (Gibco). Confluent ceils from the second passage were washed three times with Hank's balanced salt solution (HBSS). The cells were then incubated with 2 ml of HBSS for 4 hr at 37° C. The supernatant containing secreted RPP was collected and stored at −70° C. until future use. The concentration of the collected supernatant was adjusted to 14.5 $\mu$g of protein/100 $\mu$l for intravitreal injection.

Pooled RPP supernatant was initially purified by anion exchange chromatography on DEAE SEPHAROSE® CL-6B (Pharmacia, Piscataway, N.J.).

Lipopolysaccharide (LPS) obtained from *E. coli* (serotype 055:85; Sigma, St. Louis, Mo.) was dissolved in phosphate buffered saline (PBS) at a concentration of 0.1 $\mu$g/ul. After the animals were anesthetized, 5 $\mu$g of LPS was injected into the vitreous cavity of the left eye of each rabbit using a Hamilton syringe with a 30 G needle. Three of these animals also received intravitral injections of 100 $\mu$l of crude RPP solution, three received purified RPP and the remaining six received 100 $\mu$l RPP, inactivated by heating at 95° C. for 30 min. The rabbits were sacrificed 42 hr after injection. Vitreous samples from the injected eyes were obtained through a small incision in the equatorial region. The superoxide in the vitreous sample was measured by the superoxide dismutase-inhibited reduction of cytochrome. The protein concentration in the vitreous was measured by the Bio-Rad protein assay (Bio-Rad Laboratories, Hercules, Calif.) using bovine serum albumin as standard. The cells infiltrating the vitreous were counted using a hemacytometer and viability was determined by trypan blue dye exclusion.

Results

Effect of crude RPP Injection

Figure 17A:
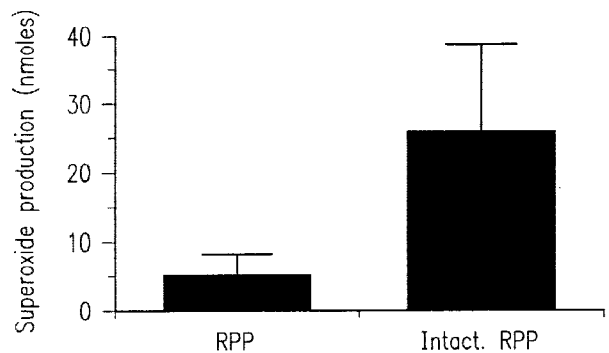
FIG. 17 graphically presents the effect of intravitreal injection of crude RPP in eyes with endotoxin induced uveitis; (a) superoxide production of vitreous in eyes injected with RPP and heat-inactivated RPP; (b) protein leakage of vitreous in eyes injected with RPP and heat-inactivated RPP; (c) cell counts of in eyes injected with RPP and heat-inactivated RPP.
Figure 17B:
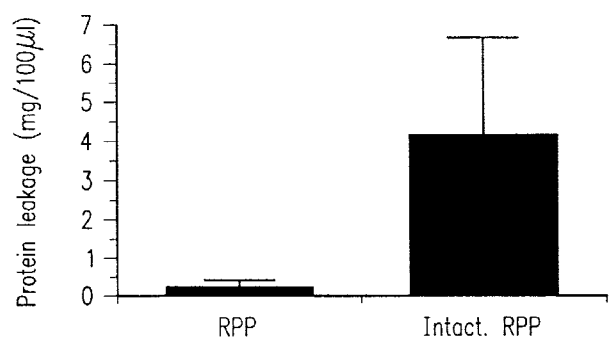
Figure 17C:
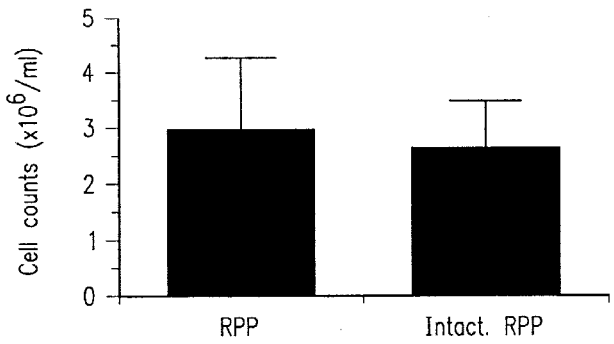

The superoxide production in 0.3 ml of vitreous was 4.83±3.52 (Mean±S.D.) nmoles and 25.67±12.75 nmoles in eyes injected with RPP and heat-inactivated RPP, respectively (FIG. 17a). This difference was statistically significant (Student's t-test ; $P<0.05$). The protein leakage was 0.29±0.13 $\mu$g/100 $\mu$l of vitreous in RPP-injected eyes and 4.15±2.38 $\mu$g/100 $\mu$l in heat-inactivated RPP-injected eyes ($P<0.05$; FIG. 17b). Cell counts (FIG. 17c) were similar in both groups, 2.96±1.34×10$^6$/ml and 2.63±0.93×10$^6$/ml for RPP and heated inactivated RPP, respectively.

Effect of Purified RPP Injection

The superoxide production in 0.3 ml of vitreous was 22.65±8.23 nmoles and 34.63±0.20 nmoles in eyes injected with the RPP and heat inactivated RPP respectively. This difference was statistically significant (Student's t-test; $P<0.05$). Cell counts were 3.88±1.10×10$^6$/ml (active) and 4.16±0.42×10$^6$/ml (inactive); the difference was not significant.

Example 4

A 75 kD Polypeptide Epitope Specifically Expressed in Retinal Pigment Epithelium Materials and Methods Isolation and Purification of RPP as Immunogen The RPE cell cultures from pigmented rabbits (Irish Farms, Norco, Calif.) were obtained and characterized as described in Example 1. All animals used for the cell culture were maintained and treated in accordance with the ARVO Resolution on the Use of Animals in Research. All RPE cultures used to obtain RPP were from either passage two or passage three. The adherent RPE cells were then incubated with Hank's balanced salt solution (HBSS) for 4 hr at 37° C. to collect secreted proteins. The pooled supernatant proteins were concentrated initially by ultrafiltration and then dialyzed against 10 mM Tris-HCl (pH 7.6) overnight. The dialyzed proteins were separated through an anion exchange column, packed with DEAE SEPHAROSE® CL-6B (Pharmacia, Piscataway, N.J.). The column was eluted with a linear gradient of 0–1 M NaCl in buffer A, 10 mM Tris-HCl (pH 7.8). The third fraction, which was previously found to be the active peak (amounting to less than 5% of the total eluates) was collected. The superoxide suppressive activity of this fraction was established before using this material as the immunogen. The PMN superoxide generation was measured by the SOD-inhibited reduction of cytochrome C.

Production of Monoclonal Antibodies

For the production of monoclonal antibody, 4 female Balb/c mice were immunized with 25 $\mu$g each of DEAE SEPHAROSE® CL-6B-purified RPP in Freund's complete adjuvant (Difco Laboratories, Detroit, Mich.). Following the initial immunization, three more boosters (25 $\mu$g each of purified RPP in Freund's incomplete adjuvant) were administered successively at 3-week intervals. Animals were bled before immunization and after the third and fourth immunizations to obtain preimmune serum and mouse anti-rabbit polyclonal antibody (pAb), respectively. Three weeks after the last booster, the mouse showing the highest titer against RPP received an intraperitoneal booster with 24 $\mu$g of purified RPP. Three days later, the mouse was sacrificed and its spleen was removed. The spleen cells were then chemically fused with Sp2/0 mouse myeloma cells using polyethylene glycol 1500 (Boehringer Mannheim, Indianapolis, Ind.). The resulting hybridoma supernatants were screened at 2 and 3 weeks for reactivity with RPP by immunoperoxidase assays on frozen rabbit eye sections. Posterior sections from both naive rabbits and rabbits injected intravitreally with 5 $\mu$g of lipopolysaccharide (*WS. typhimurium;* Difco) were used for screening. The positive cultures were expanded and retested and 14 positive hybridoma lines were selected. Subsequent subcloning of one of the lines (2B8) with the highest titer was carried out by limiting dilution on thymocyte feeder layers.

Immunohistochemistry

Rabbit, human, and bovine eyes were used for immunohistochemical analysis of RPP. Frozen sections of either whole eyes or posterior segments of the globe were cut in 7 $\mu$m sections. All cryostat sections were fixed in acetone for 5 min at 4° C., and washed with 0.01 M phosphate-buffered saline (PBS). For staining with either pAb mouse anti-rabbit RPP (1:5000) or mAb supernatant (no dilution), the primary antibody was incubated overnight at room temperature before reacting with the secondary antibody, biotinylated goat anti-mouse IgG (1:200; Dako Corporation, Santa Barbara, Calif.), for 2 hr at room temperature. To reduce nonspecific binding, all tissue sections were blocked for 20 min with 2% goat serum and 2% bovine serum albumin in PBS. For staining both rabbit and rat RPE cultures, either primary or passage-one cultures were plated on 8-well chamber slides (Lab-Tek) and grown to near confluence. The RPE cultures were similarly fixed, blocked, and reacted with the primary and secondary antibodies in a manner similar to that used for the tissue sections. Visualization for all staining was carried out by reacting first with an avidin-biotin complex (Vector laboratories, Burlingame, Calif.) and then with a substrate, 3-amino-9-ethyl carbazole (Sigma, St. Louis, Mo.). Negative controls were incubated with PBS in place of primary antibodies.

Sodium Dodecyl Sulfate-Polyacrylamide Gel Electrophoresis and Immunoblot Analysis The total protein from rabbit RPE culture supernatant was resolved by SDS-PAGE performed in a 1.5 mm thickness minigel format (Hoefer Scientific, SE 250, San Francisco, Calif.). The separating gel and stacking gel were 7.5% and 4% of polyacrylamide respectively. The SDS-buffer system used was according to that of Laemmli (1970). The following prestained molecular weight standards were used (Bio-Rad, Hercules, Calif.): myosin, 205,000; β-galactosidase, 140,000; bovine serum albumin, 83,000; carbonic anhydrase, 45,000; soybean trypsin inhibitor, 32,000; lysozyme, 18,000; and aprotinin, 7,500.

Following SDS-PAGE, the proteins separated were transferred to a polyvinylidene difluoride (PVDF) membrane (Millipore, Bedford, Mass.) using a mini trans-blot electrophoretic transfer cell (Bio-Rad) at constant 250 mA. The transfer efficiency was verified by visualizing the PVDF-bound proteins with 0.5% Ponceau S (Sigma) in water and by staining the remaining polyacrylamide gel with 0.05% Coomassie blue (Bio-Rad) solution.

For immunoprobing, the protein-bound PVDF strips were first equilibrated by immersing in 0.1% (v/v) Tween 20 in 50 mM Tris-buffered saline (TTBS, pH 7.5) for 2 hr. The strips were then incubated with either mouse preimmune serum (1:1000, 2 hr), pAb mouse anti-rabbit RPP (1:1000, 2 hr), or mAB anti-rabbit RPP (no dilution, 4 hr) at room temperature. Specifically bound antibodies were detected through an incubation with biotinylated goat anti-mouse Ig (1:500 dilution, 1.5 hr for pAb; 1:50 dilution, 2.5 hr for mAb). Visualization of bound antigen was carried out by reacting first with an avidinbiotin complex (Vector) and then with a chromogenic substrate, 3,3-diaminobenzidine tetrachloride (Sigma) and $NiCl_2$ (Sigma) solution.

Blocking of RPP Activity by Antibodies

The details on the assay for PMN superoxide production by the SOD-inhibited cytochrome C reduction have been described in Experiment 1. For testing the blocking of RPP activity by anti-RPP antibodies, the basic assay included the following four categories of tubes: 1) PMN's with 10 µl of SOD, 2) PMN's with 10 µl of water, 3) PMN's, 10 µl of water and RPP, and 4) PMN's, 10 µl of water, RPP and antibodies. Exactly 50 µl of cytochrome C (30 mg/ml, Sigma) and 75 µl of N-formyl-methionyl-leucylphenylalanine (fMLP, 4.4 µg/ml, Sigma) were added to each tube. The final concentrations of cytochrome C and fMLP in the incubation mixture were 80 µM and 0.5 µM, respectively. The total volume in the incubation mixture was 1.5 ml and the incubation was carried out at 37° C. for the desired length of time. The reduced cytochrome C was measured in a double-beam spectrophotometer (UV-160, Shimadzu, Kyoto, Japan) at 550 nm using SOD-containing sample as the reference. The molar extinction coefficient used for this measurement was 21,000 $M^{-1}cm^{-1}$.

Results

Production of Antibodies

For use as an immunogen, the crude proteins secreted by the cultured rabbit RPE cells were purified through a DEAE SEPHAROSE® CL-6B column, an anion exchanger, and a small active peak eluted near an elution volume of 370 ml was collected. This fraction amounted to less than 5% of the total proteins eluted. The superoxide inhibitory activity on this fraction was tested before it was used to produce antibodies. The immunization and subsequent fusion of spleen cells with myeloma cells yielded more than 400 hybridoma clones that secreted antibodies binding to cells within the eye. Following retesting of these clones, 14 hybridoma lines were isolated initially. The screening was carried out by immunoperoxidase assay on frozen rabbit eye sections. The use of eye sections made it possible to detect if the antibody reacted with other tissues in the eye. Two of these lines reacted strongly to RPE in the tissue and were subcloned by limited dilution. Single clones with high antibody titer to RPE were isolated from one of the lines (designated as mAb 2B8). Antibodies secreted from these single clones appeared to be similar in their properties. Antisera produced by two of the immunized Balb/c mice also produced high antibody titers with specificity toward RPE.

Characterization of Antibodies

The initial characterization of the pAb was carried out using an indirect enzyme linked immunosorbent assay (ELISA) with purified RPP as the coating antigen. It was found that the mouse pAb bound selectively to RPP and that two mice among four injected exhibited good binding to RPP up to 1:8000 dilution.

On the immunoblot analysis, the mAb was found to react to a single protein derived from the total RPE supernatant proteins. The molecular weight of this band was estimated to be 75 kD by the accompanying molecular weight standards and the corresponding relative mobility values (FIG. 18, lanes 1 and 2). In the same analysis, the pAb also reacted to this protein, giving a relatively intense band; a weaker minor band with molecular weight of 38 kD is also visible. The preimmune serum displayed no discernible band under the same condition (FIG. 18, lane 3).

Both the pAb and the mAb were found to abolish the effect of RPP. The culture supernatants collected from the confluent RPE cultures typically gave an average of 5 µg/ml of total secreted proteins. RPP amounted to approximately 5% of these total secreted proteins. Incubation of this amount of RPP with 8 to $9 \times 10^5$ PMN's typically inhibits 60 to 70% of the production of superoxide by PMN's activated by fMLP. Co-incubation of this quantity of RPP with 60 µl of mAb (in hybridoma medium containing 1% serum) for 45 min appeared to abolish the effect of RPP significantly; the PMN superoxide production displayed in the presence of RPP/mAb was 85 to 90% of the control value, compared to 40% for RPP alone. Under the same conditions, the hybridoma medium plus 1% serum gave no effect on RPP activity (FIG. 2). Similarly, co-incubation of RPP with 2 µl of pAb also abolished most of the suppressive effect of RPP. The PMN superoxide produced was 90% or more of the control value with the PMN only in the incubation mixture (FIG. 19).

Tissue and Species Specificity of Antibodies

The reactivity of antibodies toward cultured cells and various tissues was evaluated by the immunoperoxidase technique. The mAbs expanded from 3 different single clones (all derived from the hybridoma line 2B8) appeared to display exactly the same specificity toward tissue types and different species. Staining of rat and rabbit cultured RPE cells with mAb revealed an intense positive staining covering the entire cytoplasm (FIG. 20). The pAb also stained cultured rabbit RPE cells similarly in the entire cytoplasm.

The reactivity of mAbs in the intact eye was evaluated on either the naive rabbits or the animals injected with lipopolysaccharide to induce mild anterior inflammation. As shown in FIG. 21, the mAbs stained intensely and specifically the entire RPE monolayers with no detectable difference in intensities between the apical and basal lateral side of RPE. The antigen recognition by these mAbs was RPE-specific: no other epithelium in the eye was stained, including epithelia of the ciliary body, iris, cornea, and lens. In particular, in FIG. 22, the nonstaining nature of the contiguous pars plana ciliary epithelia was compared with the RPE. Human and bovine eye were among the other species tested with mAbs, which revealed positive staining of the RPE. In these species, RPE also stained intensely and specifically with this mAb. A number of nonocular tissues in rabbit were also tested for the cross-reactivity with this mAb. The organs tested included cerebrum, cerebellum, pineal gland, lung, heart, liver, spleen, kidney, pancreas, jejunum, skin, striated muscle, and aortal smooth muscles; none of these were stained. The pAbs also immunolabelled RPE in the tissue sections intensely, except that some minor reactivity with the choroidal cells was also noted (data not shown). The controls with either preimmune serum or PBS in place of primary antibody were negative.

The previously described present invention has many advantages. The advantages include the discovery of a novel retinal pigment epithelial protective proteins and biologically active variants thereof, and methods for isolating and purifying them in a simple, fast, efficient manner with high yields. The versatility and the applications of this protein, makes RPP especially valuable for their use in inhibiting oxygen metabolite production associated with tissue inflammation.

Although the present invention has been described in considerable detail with reference to certain preferred versions, other versions are possible. Thus, the spirit and scope of the appended claims should not be limited to the description of the preferred versions contained herein.

All publications and patent applications mentioned in this Specification are herein incorporated by reference to the same extent as if each of them had been individually indicated to be incorporated by reference.

What is claimed is:

1. An isolated protein secreted by retinal pigment epithelium, selected from the group consisting of proteins having molecular masses of about: 69-, and 75-kDa.

2. A protein according to claim 1, said protein containing amino acid sequences as set forth in SEQ ID NOs. 1–8.

3. A protein consisting essentially of purified soluble retinal pigment epithelial protective protein selected from the group consisting of proteins having molecular masses of about 69- and 75-kDa, wherein said protective protein suppresses the production of superoxide by phagocytes.

4. A recombinant protein according to claim 3.

5. A protein according to claim 3, having at least one amino acid sequence selected from the group consisting of SEQ ID Nos. 1–8.

6. A protein according to claim 3, which immunoreacts with antibody to retinal pigment epithelial cells.

7. The protein of claim 3 wherein the retinal pigment epithelial protective protein is from a mammal.

8. The protein of claim 7 wherein the mammal is selected from the group consisting of rabbit, mouse, rat, cattle and human.

9. A substantially pure soluble retinal pigment epithelial protective protein having a molecular mass of about: 69- or 75-kDa, said protein containing amino acid sequences as set forth in SEQ ID Nos. 1–8.

10. A recombinant soluble retinal pigment epithelial protective protein containing amino acid sequences as set forth in SEQ ID Nos 1–8, wherein said protective protein suppresses the production of superoxide by phagocytes and immunoreacts with antibody to retinal pigment epithelial cells.

11. The recombinant protein of claim 10, wherein the protein is unglycosylated or deglycosylated.

12. A purified and isolated peptide of soluble retinal pigment epithelial protective protein having an amino acid sequence selected from the group consisting of SEQ ID NOS: 1–8.

13. A recombinant peptide according to claim 12.

\* \* \* \* \*

SEQUENCE LISTING

<160> NUMBER OF SEQ ID NOS: 8

<210> SEQ ID NO 1
<211> LENGTH: 17 amino acids
<212> TYPE: PRT
<213> ORGANISM: Oryctolagus cuniculus
<220> FEATURE:
<221> NAME/KEY: Unsure
<222> LOCATION: 10
<223> OTHER INFORMATION: Author is unsure of the exact amino acid
      sequence at these positions

<400> SEQUENCE: 1

Met Gly Ile Glu Leu Tyr Gly Tyr Tyr Xaa Xaa Ser Ala Leu Gly Glu Lys
                5                   10                  15

<210> SEQ ID NO 2
<211> LENGTH: 17 amino acids
<212> TYPE: PRT
<213> ORGANISM: Oryctolagus cuniculus
<220> FEATURE:
<221> NAME/KEY: Unsure
<222> LOCATION: 15
<223> OTHER INFORMATION: Author is unsure of the exact amino acid
      sequence at this position

<400> SEQUENCE: 2

Asn Gln Asn Lys Val Gln Lys Gln Ala Asn Met His Met Gln Xaa Tyr Leu
                5                   10                  15

<210> SEQ ID NO 3
<211> LENGTH: 25 amino acids
<212> TYPE: PRT
<213> ORGANISM: Oryctolagus cuniculus

<400> SEQUENCE: 3

Ala Phe Ser Asn Asn Glu Ala Asp Ala Val Thr Leu Asp Gly Gly
                5                   10                  15

Leu Val Tyr Glu Ala Gly Leu Ser Pro Asn
                20                  25

```
<210> SEQ ID NO 4
<211> LENGTH: 10 amino acids
<212> TYPE: PRT
<213> ORGANISM: Oryctolagus cuniculus

<400> SEQUENCE: 4

Phe Leu Val Leu Asn Lys Thr Val Val Gly
                 5                  10

<210> SEQ ID NO 5
<211> LENGTH: 13 amino acids
<212> TYPE: PRT
<213> ORGANISM: Oryctolagus cuniculus

<400> SEQUENCE: 5

Gly Tyr Leu Ala Val Ala Val Val Ile Ser Leu Gly Ser
                 5                  10

<210> SEQ ID NO 6
<211> LENGTH: 10 amino acids
<212> TYPE: PRT
<213> ORGANISM: Oryctolagus cuniculus

<400> SEQUENCE: 6

Ser Ala Glu Leu Asn Lys Phe Met Gly Arg
                 5                  10

<210> SEQ ID NO 7
<211> LENGTH: 21 amino acids
<212> TYPE: PRT
<213> ORGANISM: Oryctolagus cuniculus
<220> FEATURE:
<221> NAME/KEY: Unsure
<222> LOCATION: 13
<223> OTHER INFORMATION: Author is unsure of the exact amino acid
      sequence at these positions

<400> SEQUENCE: 7

Glu Leu Val Glu Ser Gly Leu Val Ala Phe Val Ser Xaa Glu Ser
                 5                  10                  15

Xaa Glu Xaa Ser Ser Pro
                 20

<210> SEQ ID NO 8
<211> LENGTH: 15 amino acids
<212> TYPE: PRT
<213> ORGANISM: Oryctolagus cuniculus
<220> FEATURE:
<221> NAME/KEY: Unsure
<222> LOCATION: 13
<223> OTHER INFORMATION: Author is unsure of the exact amino acid
      sequence at these positions

<400> SEQUENCE: 8

Gly Tyr Leu Ala Leu Pro Ala Phe Gln Ser Leu Gly Xaa Xaa Asn
                 5                  10                  15
```